(12) United States Patent
Park et al.

(10) Patent No.: US 10,335,114 B2
(45) Date of Patent: Jul. 2, 2019

(54) METHOD AND ULTRASOUND APPARATUS FOR PROVIDING ULTRASOUND IMAGE

(71) Applicant: SAMSUNG MEDISON CO., LTD., Hongcheon-gun (KR)

(72) Inventors: Sung-chan Park, Suwon-si (KR); Jung-ho Kim, Yongin-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 450 days.

(21) Appl. No.: 15/185,965

(22) Filed: Jun. 17, 2016

(65) Prior Publication Data
US 2017/0143295 A1 May 25, 2017

(30) Foreign Application Priority Data

Nov. 25, 2015 (KR) .......................... 10-2015-0165571

(51) Int. Cl.
*A61B 8/00* (2006.01)
*A61B 8/08* (2006.01)
*A61B 17/34* (2006.01)

(52) U.S. Cl.
CPC ............ *A61B 8/0841* (2013.01); *A61B 8/461* (2013.01); *A61B 8/5207* (2013.01); *A61B 8/5246* (2013.01); *A61B 8/5253* (2013.01); *A61B 8/54* (2013.01); *A61B 2017/3413* (2013.01)

(58) Field of Classification Search
None
See application file for complete search history.

(56) References Cited

U.S. PATENT DOCUMENTS

| 8,348,848 | B1 | 1/2013 | Tamura |
| 8,663,110 | B2 | 3/2014 | Kim et al. |
| 9,226,729 | B2 | 1/2016 | Tashiro et al. |
| 9,326,750 | B2 | 5/2016 | Takeda et al. |
| 2001/0044580 | A1* | 11/2001 | Pellegretti ................ A61B 8/06 600/437 |
| 2011/0249878 | A1* | 10/2011 | Pagoulatos .......... A61B 8/0841 382/131 |

(Continued)

FOREIGN PATENT DOCUMENTS

JP 2012-120747 A 6/2012
JP 2012-192162 A 10/2012

(Continued)

OTHER PUBLICATIONS

Communication dated Apr. 25, 2017, issued by the European Patent Office in counterpart European Application No. 16173453.8.

(Continued)

*Primary Examiner* — Jonathan Cwern
(74) *Attorney, Agent, or Firm* — Sughrue Mion, PLLC

(57) ABSTRACT

A method of providing an ultrasound image via an ultrasound apparatus including a medical tool that is inserted into an object, the method includes: obtaining a plurality of steering images corresponding to a plurality of steering angles, selecting one of the plurality of steering images based on brightness information of the medical tool in each of the plurality of steering images, detecting a steering angle corresponding to the selected steering image, obtaining an ultrasound image including the medical tool by using the detected steering angle, and displaying the obtained ultrasound image on a screen.

29 Claims, 20 Drawing Sheets

(56) References Cited

U.S. PATENT DOCUMENTS

| | | | |
|---|---|---|---|
| 2012/0253181 A1 | 10/2012 | Okamura et al. | |
| 2013/0274608 A1 | 10/2013 | Takeda et al. | |
| 2014/0155738 A1 | 6/2014 | Cheny et al. | |
| 2014/0187942 A1 | 7/2014 | Wang et al. | |
| 2015/0351717 A1 | 12/2015 | Tashiro et al. | |
| 2016/0081666 A1* | 3/2016 | Deguchi | A61B 8/0841 600/424 |
| 2016/0317118 A1* | 11/2016 | Parthasarathy | A61B 8/0841 |

FOREIGN PATENT DOCUMENTS

| | | |
|---|---|---|
| JP | 2013-192627 A | 9/2013 |
| JP | 2015-043824 A | 3/2015 |
| KR | 10-1143663 B1 | 5/2012 |

OTHER PUBLICATIONS

Cheung S et al: "Enhancement of Needle Visibility in Ultrasound-Guided Percutaneous Procedures", Ultrasound in Medicine and Biology, vol. 30, No. 5, May 1, 2004 (May 1, 2004), pp. 617-624, XP004515003, (8 pages total).

Chin K J et al: "Needle Visualization in Ultrasound-Guided Regional Anesthesia: Challenges and Solutions", Regional Anesthesia and Pain Medicine, vol. 33, No. 6, Nov. 1, 2008 (Nov. 1, 2008), pp. 532-544, XP025583269, (13 pages total).

\* cited by examiner

FIG. 8
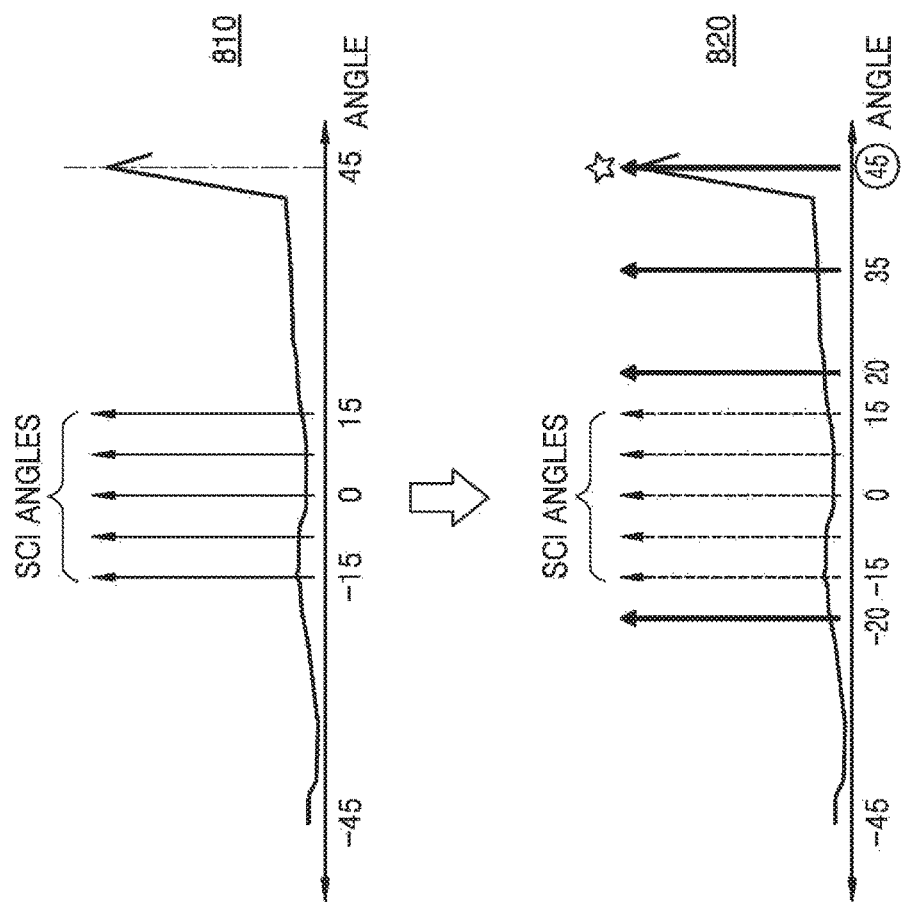
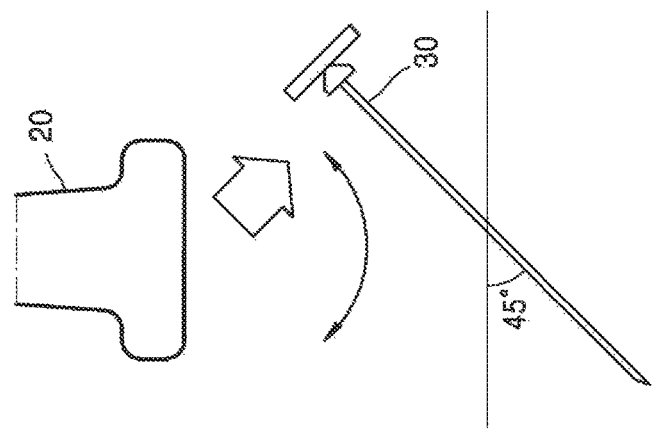

FIG. 10
Coarse Search (S1010)
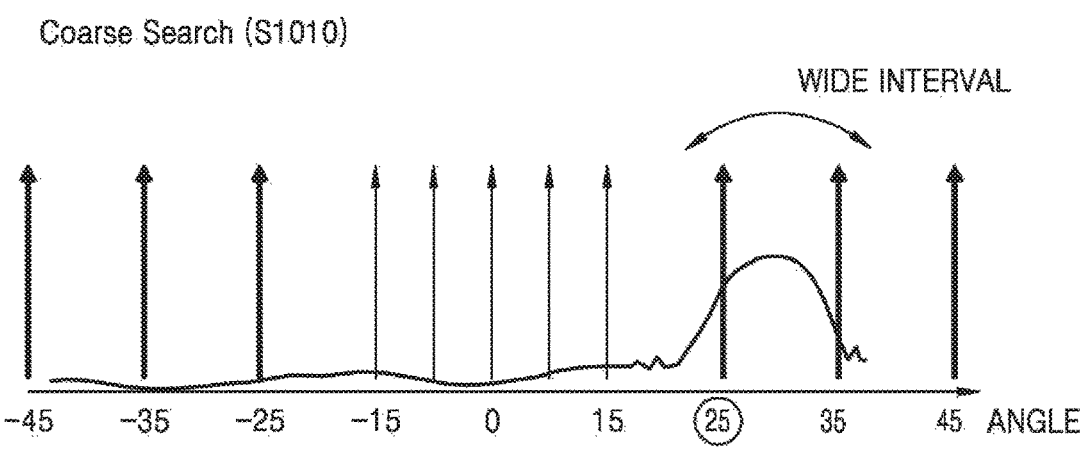
Fine Search (S1020)
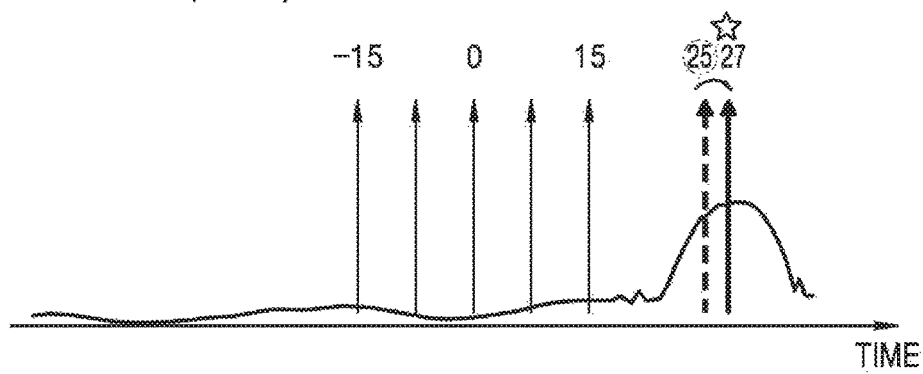

FIG. 17
 
1710 (SCI)     1720 (COMBINED IMAGE)
FIG. 18
 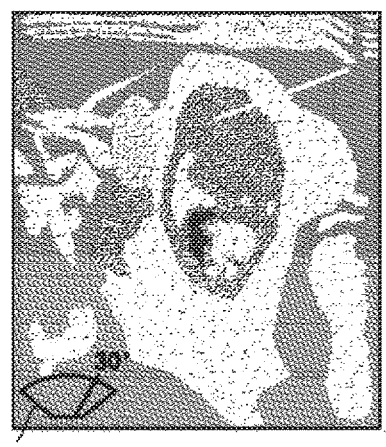
1810 (SCI)     1820 (COMBINED IMAGE)

METHOD AND ULTRASOUND APPARATUS FOR PROVIDING ULTRASOUND IMAGE

CROSS-REFERENCE TO RELATED APPLICATION

This application claims the benefit of Korean Patent Application No. 10-2015-0165571, filed on Nov. 25, 2015, in the Korean Intellectual Property Office, the disclosure of which is incorporated herein in its entirety by reference.

BACKGROUND

1. Field

The present disclosure relates to methods and ultrasound apparatuses for providing an ultrasound image including a medical tool (for example, a needle) inserted into a human body.

2. Description of the Related Art

An ultrasound diagnosis apparatus transfers an ultrasound signal from a body surface of an object to a predetermined portion inside the body, and obtains an image of a cross-section of a soft tissue or blood flow based on information of an ultrasound signal reflected by an internal tissue.

The ultrasound diagnosis apparatus is compact and inexpensive, and can display an image in real-time. Also, the ultrasound diagnosis apparatus does not expose users to X-rays, etc. and thus is very safe, and accordingly, is widely used together with other imaging diagnosis apparatuses such as an X-ray diagnosis apparatus, a computerized tomography (CT) scanner, a magnetic resonance image (MRI) apparatus, and a nuclear medical diagnosis apparatus.

Generally, for diagnosing a tumor, an ultrasound biopsy is performed by cutting a portion of a patient's tissue and directly observing the cut tissue with the naked eyes or by using a microscope. During the biopsy, an operator should be able to detect a trajectory of a needle and the accurate location of a needle end.

SUMMARY

Provided are methods and ultrasound apparatuses for providing a clear ultrasound image including a medical tool by adaptively detecting a steering angle in order to increase sensitivity of an ultrasound image of the medical tool (for example, a needle) having a characteristic of regular reflection.

Additional aspects will be set forth in part in the description which follows and, in part, will be apparent from the description, or may be learned by practice of the presented exemplary embodiments.

According to an aspect of an exemplary embodiment, a method of providing an ultrasound image comprising a medical tool that is inserted into an object, performed by an ultrasound apparatus, the method includes: obtaining a plurality of steering images corresponding to a plurality of steering angles; selecting one of the plurality of steering images based on brightness information of the medical tool in each of the plurality of steering images; detecting a steering angle corresponding to the selected steering image; obtaining an ultrasound image including the medical tool by using the detected steering angle; and displaying the obtained ultrasound image on a screen.

According to an aspect of another exemplary embodiment, a method of providing a needle ultrasound image includes: obtaining a plurality of steering images corresponding to a plurality of steering angles; detecting a needle in each of the plurality of steering images; selecting one of the plurality of steering images based on brightness information of a needle in each of the plurality of steering images; detecting a steering angle corresponding to the selected steering image; obtaining a needle ultrasound image by using the detected steering angle; and displaying the obtained needle ultrasound image on a screen.

The obtaining of the plurality of steering images may include: obtaining first steering images corresponding to first steering angles defined in advance and used for generating a spatial compound image (SCI).

The obtaining of the plurality of steering images may further include: obtaining the spatial compound image based on the first steering images.

The obtaining of the ultrasound image may include: generating an ultrasound image including the medical tool by combining a steering image obtained at the detected steering angle with the spatial compound image.

The selecting of one of the plurality of steering images may include: selecting candidate steering images including the medical tool having a brightness value greater than a threshold value from among the plurality of steering images, based on the brightness information of the medical tool in each of the plurality of steering images; and selecting one steering image including the medical tool having a highest brightness value from among the candidate steering images.

The selecting of one of the plurality of steering images may include: selecting one steering image including the medical tool having a highest brightness value, based on the brightness information of the medical tool in each of the plurality of steering images.

The selecting of one of the plurality of steering images may include: when a brightness value of a medical tool in each of the first steering images is equal to or less than a threshold value, selecting a second steering angle different from the first steering angles; and when a brightness value of a medical tool in a second steering image corresponding to the second steering angle is greater than the threshold value, selecting the second steering image, and the displaying of the obtained ultrasound image may include: displaying a second ultrasound image obtained at the second steering angle.

The selecting of one of the plurality of steering images may further include: when the brightness value of the medical tool in the second steering image is equal to or less than the threshold value, selecting a third steering angle different from the first steering angles and the second steering angle; and when a brightness value of the medical tool in a third steering image corresponding to the third steering angle is greater than the threshold value, selecting the third steering image.

The obtaining of the ultrasound image may include: selecting a fourth steering image and a fifth steering image each including a medical tool having a brightness value greater than a first threshold value and less than a second threshold value from among the plurality of steering images; determining a particular steering angle between a fourth steering angle corresponding to the fourth steering image and a fifth steering angle corresponding to the fifth steering image; and obtaining the ultrasound image including the medical tool by using the determined particular steering angle.

The selecting of one of the plurality of steering images may include: selecting a sixth steering image including a medical tool having a highest brightness value from among the plurality of steering images; when a brightness value of the medical tool in the sixth steering image is equal to or less than a threshold value, selecting a seventh steering angle within a predetermined angle range based on a sixth steering angle corresponding to the sixth steering image; and when a brightness value of a medical tool in a seventh steering image corresponding to the seventh steering angle is greater than the threshold value, selecting the seventh steering image, and the displaying of the obtained ultrasound image may include: displaying a seventh ultrasound image obtained at the seventh steering angle.

The predetermined angle range may increase when an angle of the sixth steering image decreases and decreases when the angle of the sixth steering image increases.

The obtaining of the plurality of steering images may include: detecting an outline of the medical tool in each of the plurality of steering images based on a difference between the plurality of steering images.

The displaying of the obtained ultrasound image may include: updating the ultrasound image in real-time based on the detected steering angle.

The method may further include: when a brightness value of a medical tool in the updated ultrasound image is equal to or less than a threshold value, determining a new steering angle; and displaying a new ultrasound image corresponding to the new steering angle.

The determining of the new steering angle may include: selecting the new steering angle within a predetermined angle range based on the detected steering angle.

According to an aspect of another exemplary embodiment, an ultrasound apparatus for providing an ultrasound image including a medical tool inserted into an object, the apparatus includes: an image processor configured to obtain a plurality of steering images corresponding to a plurality of steering angles; a controller configured to select one of the plurality of steering images based on brightness information of the medical tool in each of the plurality of steering images, detect a steering angle corresponding to the selected steering image, and obtain an ultrasound image including the medical tool based on the detected steering angle; and a display configured to display the obtained ultrasound image including the medical tool.

According to an aspect of another exemplary embodiment, an ultrasound apparatus includes: an image processor configured to obtain a plurality of steering images corresponding to a plurality of steering angles, and detect a needle in each of the plurality of steering images; a controller configured to select one of the plurality of steering images based on brightness information of the needle in each of the plurality of steering images and detect a steering angle corresponding to the selected steering image; and a display configured to display a needle ultrasound image obtained by using the detected steering angle.

The plurality of steering images may include: first steering images corresponding to first steering angles defined in advance and used for generating a spatial compound image (SCI).

The image processor may be further configured to obtain the spatial compound image based on the first steering images.

The image processor may be further configured to generate an ultrasound image including the medical tool by combining a steering image obtained at the detected steering angle with the special compound image.

The controller may be further configured to select candidate steering images including the medical tool having a brightness value greater than a threshold value from among the plurality of steering images based on the brightness information of the medical tool in each of the plurality of steering images, and to select one steering image including the medical tool having a highest brightness value from among the candidate steering images.

The controller may be further configured to select one steering image including the medical tool having a highest brightness value based on the brightness information of the medical tool in each of the plurality of steering images.

The controller may be further configured to select a second steering angle different from the first steering angles when a brightness value of a medical tool in each of the first steering images is equal to or less than a threshold value, and to generate a second ultrasound image based on the second steering angle when a brightness value of a medical tool in a second steering image corresponding to the second steering angle is greater than the threshold value.

The controller may be further configured to select a fourth steering image and a fifth steering image each including a medical tool having a brightness value greater than a first threshold value and less than a second threshold value from among the plurality of steering images, to determine a particular steering angle between a fourth steering angle corresponding to the fourth steering image and a fifth steering angle corresponding to the fifth steering image, and to obtain the ultrasound image including the medical tool based on the particular steering angle.

The controller may be further configured to select a sixth steering image including a medical tool having a highest brightness value from among the plurality of steering images, select a seventh steering angle within a particular angle range based on a sixth steering angle corresponding to the sixth steering image when a brightness value of the medical tool in the sixth steering image is equal to or less than a threshold value, and to control the display to display a seventh ultrasound image obtained based on the seventh steering angle when a brightness value of a medical tool in a seventh steering image corresponding to the seventh steering angle is greater than the threshold value.

The predetermined angle range may increase when an angle of the sixth steering image decreases and decreases when the angle of the sixth steering image increases.

The image processor may include an outline detector configured to detect an outline of the medical tool in each of the plurality of steering images based on a difference between the plurality of steering images.

The controller may be further configured to update the ultrasound image in real-time based on the detected steering angle.

The controller may be further configured to determine a new steering angle when a brightness value of a medical tool in the updated ultrasound image is equal to or less than a threshold value and to control the display to display a new ultrasound image corresponding to the new steering angle.

The controller may be further configured to determine the new steering angle within a predetermined angle range based on the detected steering angle.

BRIEF DESCRIPTION OF THE DRAWINGS

These and/or other aspects will become apparent and more readily appreciated from the following description of the exemplary embodiments, taken in conjunction with the accompanying drawings in which:

FIG. 8 is a diagram for explaining an operation of detecting, at an ultrasound apparatus, a steering angle in the case where an incident angle of a needle is 45 degrees;

FIG. 10 is a diagram for explaining an operation of adaptively detecting, at an ultrasound apparatus, a steering angle;

FIGS. 17 to 20 are diagrams for explaining an indication representing a kind of an ultrasound image displayed on a screen.

DETAILED DESCRIPTION

Figure 1:
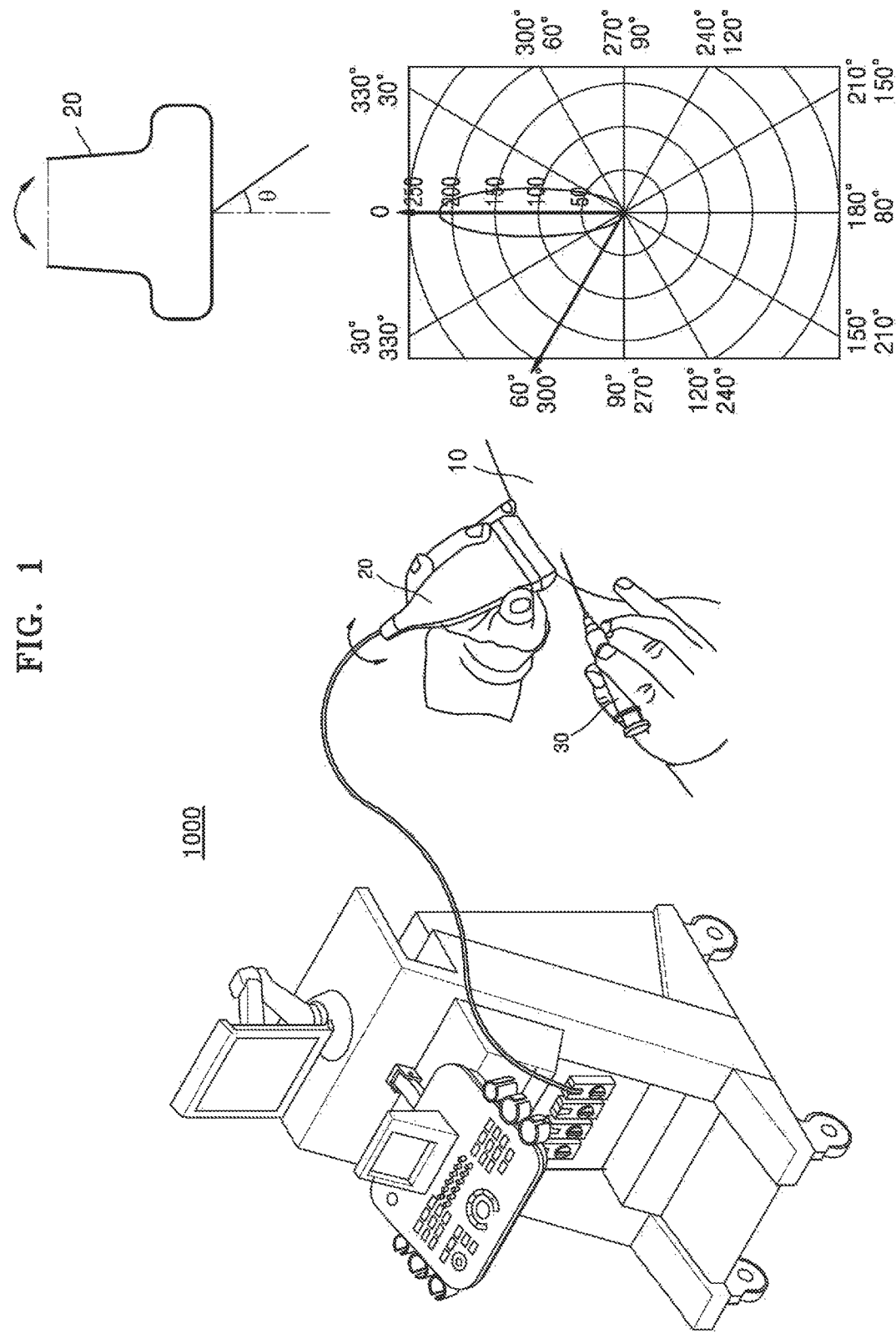
FIG. 1 is a diagram for explaining an ultrasound system according to an embodiment.

The terms used in this specification are those general terms currently widely used in the art in consideration of functions of the inventive concept, but the terms may vary according to the intention of one of ordinary skill in the art, case precedents, or the occurrence of new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" denotes an image of an object obtained by using an ultrasound signal. The object may denote a portion of a body. For example, the object may be a liver, a heart, a brain, a breast, an abdomen, nuchal translucency (NT), delts, a fetus, etc.

Also, in the present specification, an ultrasound image may be variously implemented. For example, an ultrasound image may include at least one of a brightness (B) mode image representing the magnitude of an ultrasound echo signal reflected by an object by using brightness, a color Doppler image expressing a velocity of a moving object in terms of colors by using a Doppler effect, a spectral Doppler image representing an image of a moving object in the form of a spectrum by using the Doppler effect, a power Doppler image expressing the intensity of a Doppler signal or a number of structures (for example, red blood cells in blood) by using color, a motion (M) mode image representing movement of an object according to time at a predetermined location, and an elastic mode image representing a reaction difference between a case of applying compression to an object and a case of not applying compression to the object in the form of an image, but is not limited thereto. Also, according to an embodiment, an ultrasound image may be a two-dimensional (2D) image, a 3D image, or a 4D image.

In the present specification, an ultrasound image may be an image including a medical tool inserted into an object. Examples of a medical tool inserted into the object may include a needle, a catheter, a scalpel, etc., but the medical tool is not limited thereto. Also, the medical tool inserted into the object may be a reflector that reflects an ultrasound signal. Hereinafter, for convenience of description, a case where the medical tool inserted into the object is a needle is described as an example.

Throughout the specification, a "user" is a medical expert and may be a doctor, a nurse, a medical laboratory technologist, a sonographer, etc., but is not limited thereto.

Reference will now be made in detail to embodiments, examples of which are illustrated in the accompanying drawings. In this regard, the present embodiments may have different forms and should not be construed as being limited to the descriptions set forth herein. Also, for clear description of the inventive concept in the drawings, portions irrelevant to description are omitted, and like reference numerals are used for like components throughout the specification.

FIG. 1 is a diagram for explaining an ultrasound system according to an embodiment.

As illustrated in FIG. 1, an ultrasound apparatus 1000 may generate an ultrasound image of an object 10 by transmitting an ultrasound signal (an ultrasound beam) to the object 10 via a probe 20 and receiving an ultrasound echo signal reflected by the object 10. In this case, according to an embodiment, the ultrasound apparatus 1000 may adjust a steering angle (for example, Θ) of the ultrasound signal transmitted via the probe 20. The probe 20 may include a convex probe, a linear probe, a 1D probe, a 2D probe, a 3D probe, etc., but is not limited thereto.

Generally, an ultrasound echo signal spreads over a wide angle regardless of a steering angle of an ultrasound signal, but an ultrasound echo signal reflected by a specular surface progresses to a specific angle. For example, since a needle 30 inserted into the object 10 may be a specular surface with respect to an ultrasound signal, an ultrasound echo signal reflected by the needle 30 progresses to a specific angle (for example, a reflection angle that is the same as an incident angle with respect to the needle 30).

Therefore, since an ultrasound signal transmitted by the probe 20 is regularly reflected by the needle 30, in the case where an ultrasound signal is incident vertically with respect to the needle 30, the intensity of an ultrasound echo signal reflected by the needle 30 may be highest. For example, when an ultrasound signal transmitted by the probe 20 is incident to the needle 30 at an incident angle of about 0 degree, the intensity of an ultrasound echo signal reflected by the needle 30 may be highest. In contrast, in the case where an ultrasound signal transmitted by the probe 20 is incident to the needle 30 at an incident angle of about 45 degrees or more, since an ultrasound echo signal is reflected by the needle 30 at a reflection angle of about 45 degrees or more, it is difficult for the probe 20 to focus an ultrasound echo signal of the needle 30. That is, the intensity of the ultrasound echo signal received from the needle 30 reduces.

Since the needle 30 may appear most clearly in an ultrasound image in the case where an ultrasound signal transmitted from the probe 20 is vertically incident to the needle 30, the ultrasound apparatus 1000 needs to adjust a steering angle of an ultrasound signal so that the ultrasound signal may be vertically incident to the needle 30. Relation between a steering angle of an ultrasound signal and a needle edge value (for example, a brightness value, an intensity value, and an intensity gradient) is described more with reference to FIG. 2.

Figure 2:
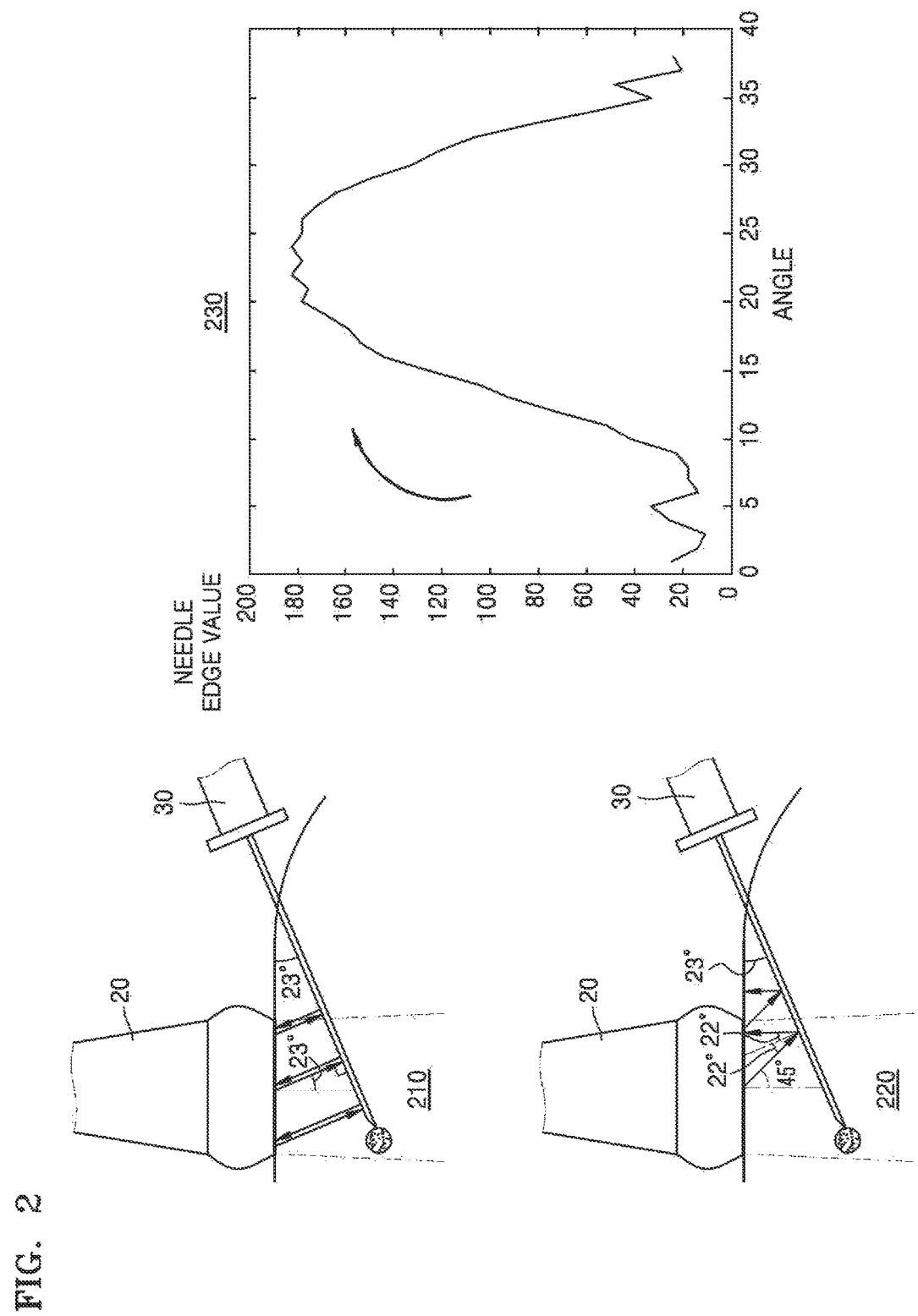
FIG. 2 is a diagram for explaining an edge (brightness) value of a needle varying with a steering angle.

FIG. 2 is a diagram for explaining an edge (brightness) value of a needle depending on a steering angle. In FIG. 2, a case where the probe 20 is located in parallel to the surface of an object, and the needle 30 is inserted at an incident angle of about 23 degrees from the surface of the object is described as an example.

According to an embodiment, a needle edge value may include at least one of a brightness value, an intensity value, and an intensity gradient value of the needle 30, but is not limited thereto.

Referring to 210 of FIG. 2, the ultrasound apparatus 1000 may transmit an ultrasound signal in which a steering angle is about 23 degrees to an object including the needle 30 inserted at an incident angle of about 23 degrees. In this case, since the transmitted ultrasound signal is incident to the needle 30 at an incident angle of about 0 degree, a reflection angle of an ultrasound echo signal reflected by the needle 30 may be also about 0 degree. In this case, since the ultrasound echo signal reflected by the needle 30 may be accurately transferred to the probe 20, the intensity of the ultrasound echo signal reflected by the needle 30 when the steering angle is about 23 degrees may be highest. For example, referring to a graph 230, in the case where the steering angle of an ultrasound signal is about 23 degrees, a needle edge value may be about 180.

Referring to 220 of FIG. 2, the ultrasound apparatus 10000 may transmit an ultrasound signal in which a steering angle is about 45 degrees to an object including the needle 30 inserted at an incident angle of about 23 degrees. In this case, since the transmitted ultrasound signal is incident to the needle 30 at an incident angle of about 22 degrees, a reflection angle of an ultrasound echo signal reflected by the needle 30 may be also about 22 degrees. In this case, since the ultrasound echo signal reflected by the needle 30 may not be accurately transferred to the probe 20, the intensity of the ultrasound echo signal reflected by the needle 30 when the steering angle is about 45 degrees may reduce compared to the case where the steering angle is about 23 degrees. For example, referring to the graph 230, in the case where the steering angle of an ultrasound signal is about 45 degrees, a needle edge value may be about 20 or less.

Consequently, due to a characteristic of regular reflection of the needle 30, in the case where a steering angle is determined such that an ultrasound signal is vertically incident to the needle 30, an ultrasound echo signal including a highest needle edge value may be obtained. For example, in the case where the probe 20 is located horizontally with respect to the surface of an object and an incident angle of the needle 30 is about 23 degrees, an ultrasound echo signal including a highest needle edge value may be obtained when a steering angle of the probe 20 is about 23 degrees. Also, in the case where an incident angle of the needle 30 is about 40 degrees, an ultrasound echo signal including a highest needle edge value may be obtained when a steering angle is about 40 degrees.

However, a user may not accurately know an incident angle of the needle 30, the probe 20 may not be fixed while being horizontal with respect to the surface of the object, and a relative angle between the probe 20 and the needle 30 changes while a user controls the probe 20. Therefore, the ultrasound apparatus 1000 should adaptively change a steering angle of an ultrasound signal in order to display a clear image of the needle 30 on a screen.

A method of providing a needle ultrasound image that clearly shows the needle 30 by detecting a steering angle in which the ultrasound apparatus 1000 allows an ultrasound signal to be vertically incident to the needle 30 is described below in detail.

Figure 3:
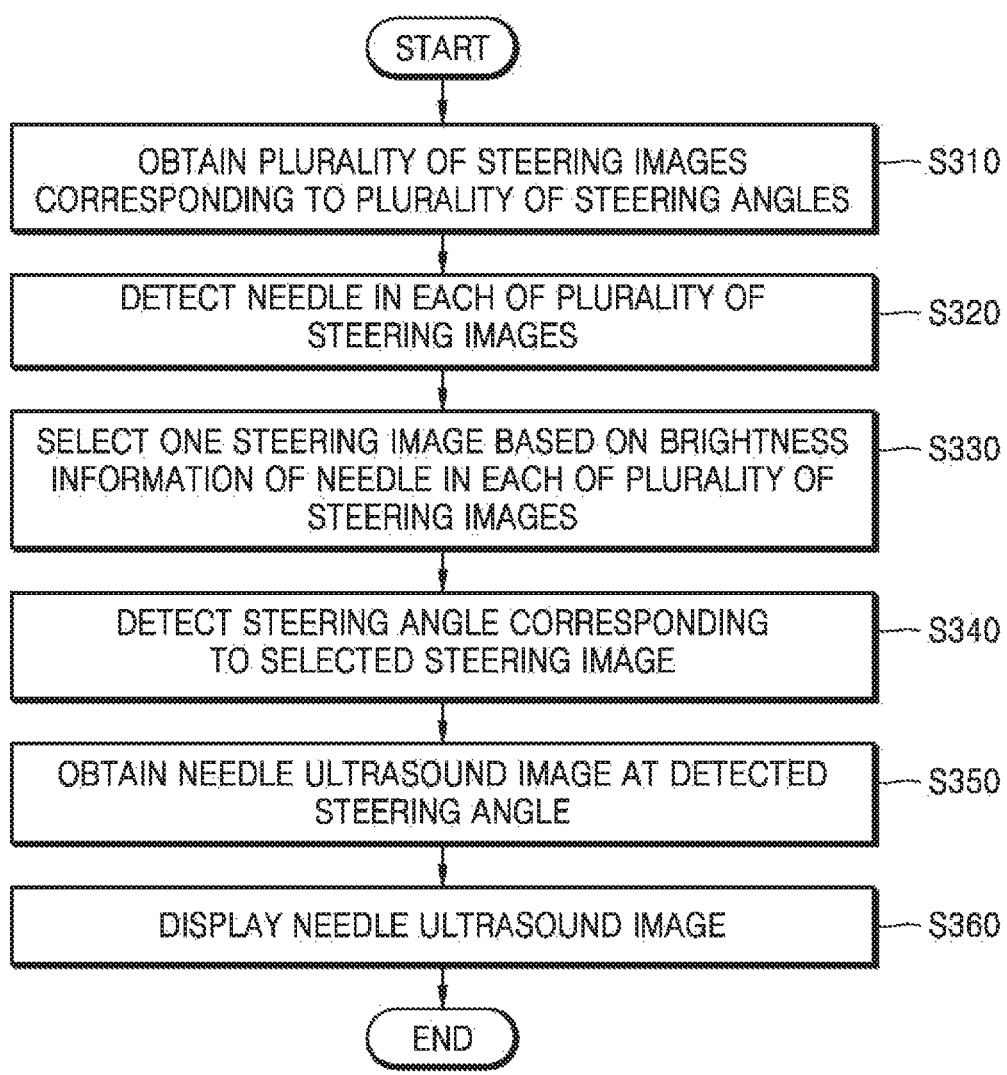
FIG. 3 is a flowchart of explaining a method of providing a needle ultrasound image via an ultrasound apparatus according to an embodiment.

FIG. 3 is a flowchart for explaining a method of providing a needle ultrasound image of an ultrasound apparatus according to an embodiment.

In operation S310, the ultrasound apparatus 1000 may obtain a plurality of steering images corresponding to a plurality of steering angles.

In the present specification, the steering image may denote an ultrasound image generated by using an ultrasound signal transmitted at a specific steering angle by the probe 20. For example, in the case where a first ultrasound image is obtained by transmitting an ultrasound signal to an object at a steering angle of about 30 degrees, the first ultrasound image may be a steering image corresponding to the steering angle of about 30 degrees.

According to an embodiment, a plurality of steering images corresponding to a plurality of steering angles may include steering images used for generating a spatial compound image (SCI), or an SCI, but are not limited thereto. The spatial compound image may be a compound image that compounds a plurality of steering images corresponding to a plurality of steering angles.

For example, the ultrasound apparatus 1000 may obtain first steering images corresponding to first steering angles defined in advance used for generating an SCI. For example, the ultrasound apparatus 1000 may obtain the first steering images respectively corresponding to −15 degrees, −10 degrees, 0 degree, 10 degrees, and 15 degrees by transmitting ultrasound signals at −15 degrees, −10 degrees, 0 degree, 10 degrees, and 15, respectively. Also, the ultrasound apparatus 1000 may generate an SCI by compounding the first steering images corresponding to −15 degrees, −10 degrees, 0 degree, 10 degrees, and 15 degrees.

Steering angles defined in advance used for generating the SCI may be various. For example, steering angles defined in advance may be (−15 degrees, −10 degrees, 0 degree, 10 degrees, and 15 degrees), may be (−20 degrees, −10 degrees, 10 degrees, and 20 degrees), may be (−25 degrees, −15 degrees, 0 degree, 15 degrees, and 25 degrees), but are not limited thereto. For convenience of description, a case where steering angles defined in advance used for generating the SCI are (−15 degrees, −10 degrees, 0 degree, 10 degrees, and 15 degrees) is described as an example.

According to an embodiment, the ultrasound apparatus 1000 may obtain steering images corresponding to other steering angles besides steering angles defined in advance. For example, in the case where the steering angles defined in advance are −15 degrees, −10 degrees, 0 degree, 10 degrees, and 15 degrees, the ultrasound apparatus 1000 may obtain steering images corresponding to 25 degrees, 35 degrees, and 45 degrees by transmitting ultrasound signals at steering angles of 25 degrees, 35 degrees, and 45 degrees, respectively.

According to an embodiment, after obtaining the steering images used for generating the SCI, the ultrasound apparatus 1000 may obtain steering images at other steering angles, and obtain steering images corresponding to arbitrary steering angles (for example, −30, −20, −10, 0, 10, 20, and 30 degrees) regardless of the SCI.

Meanwhile, according to an embodiment, the ultrasound apparatus 1000 may include a first beamformer for generating an SCI and a second beamformer for generating a steering image. In this case, the first beamformer and the second beamformer may be implemented as one beamforming apparatus, and implemented as separate beamforming apparatuses. Also, according to an embodiment, the first beamformer and the second beamformer may perform multi-line beam forming or plane wave beam forming, but are not limited thereto.

In operation S320, the ultrasound apparatus 1000 may detect a needle in each of the plurality of steering images. The detecting of the needle 30 may include detecting the outline of the needle 30. The detecting of the needle 30 may be performed by using various known methods.

For example, the ultrasound apparatus 1000 may detect a linear portion from each steering image as the outline of the needle 30 by using a characteristic that the needle 30 has a linear form.

Also, as described above, since a brightness value of the needle 30 changes depending on a steering angle, the ultrasound apparatus 1000 may detect a portion in which a brightness value changes as the outline of the needle 30 by comparing the plurality of steering images.

Meanwhile, the ultrasound apparatus 1000 may select a first image having a lowest brightness value of the needle 30 and a second image having a highest brightness value of the needle 30 from among the plurality of steering images, and generate a difference image between the first image and the second image. In this case, since a tissue has a constant brightness regardless of a steering angle, the rest of portions except the needle 30 in the difference image may appear as a black color, and only the needle portion may appear bright.

Therefore, the ultrasound apparatus 1000 may verify whether detection of the needle 30 in each steering image is accurate. For example, the ultrasound apparatus 1000 may determine whether the location of a portion appearing bright in the difference image coincides with the location of the needle 30 detected from each steering image. The difference image is described below more with reference to FIG. 5.

In operation S330, the ultrasound apparatus 1000 may select one steering image from among the plurality of steering images based on brightness information of the needle in each of the plurality of steering images.

According to an embodiment, the ultrasound apparatus 1000 may select a steering image including the needle 30 having a brightness value greater than a threshold value. Here, the brightness value may include intensity and an intensity gradient, but is not limited thereto.

For example, the ultrasound apparatus 1000 may select a first steering image including the needle 30 having a brightness value greater than the threshold value (for example, 150) from among the plurality of steering images.

Meanwhile, in the case where all of the plurality of steering images corresponding to the plurality of steering angles obtained in operation S310 include the needle 30 having a brightness value equal to or less than the threshold value, the ultrasound apparatus 1000 may determine a new steering angle to generate a new steering image including the needle 30 having a brightness value greater than the threshold value (for example, 150). Also, the ultrasound apparatus 1000 may select a new steering image corresponding to the new steering angle. An operation of determining, at the ultrasound apparatus 1000, the new steering angle is described below in more detail with reference to FIG. 7.

According to an embodiment, the ultrasound apparatus 1000 may select a steering image including the needle 30 having a highest brightness value from among the plurality of steering images. For example, in the case where a first steering image, a second steering image, and a third steering image include the needle 30 having a brightness value greater than the threshold value, the ultrasound apparatus 1000 may select the first steering image including the needle 30 having a highest brightness value from among the first steering image, the second steering image, and the third steering image.

Meanwhile, in the case where all of the plurality of steering images corresponding to the plurality of steering angles obtained in operation S310 include the needle 30 having a brightness value equal to or less than the threshold value, the ultrasound apparatus 1000 may select a fourth steering image including the needle 30 having a highest brightness value from among the plurality of steering images. Also, the ultrasound apparatus 1000 may detect a new steering angle within a predetermined angle range (for example, ±10) from a fourth steering angle (for example, 30 degrees) used for obtaining the fourth steering image. For example, the ultrasound apparatus 1000 may determine a new steering angle (for example, 37 degrees) to generate a new steering image including the needle 30 having a brightness value greater than the threshold value.

In this case, the predetermined angle range for detecting the new steering angle may increase when the fourth steering angle reduces, and may reduce when the fourth steering angle increases. The predetermined angle range for detecting the new steering angle is described below in detail with reference to FIGS. 9 and 11.

In operation S340, the ultrasound apparatus 1000 may detect a steering angle corresponding to the selected steering image.

For example, in the case where the selected steering image is an ultrasound image generated by using a steering angle of about 30 degrees, the ultrasound apparatus 1000 may detect a steering angle corresponding to the selected steering image as '30 degrees'.

According to an embodiment, an absolute value of the detected steering angle may be an angle less than an absolute value of a maximum steering angle provided by the ultrasound apparatus 1000 (for example, |maximum steering angle|>|detected steering angle|). For example, in the case where a steering angle provided by the ultrasound apparatus 1000 is between about −90 degrees and about +90 degrees (that is, an absolute value of a maximum steering angle is about 90), a detected steering angle may be between about −45 degrees and about +45 degrees.

Meanwhile, according to an embodiment, the ultrasound apparatus 1000 may select a plurality of steering images, and determine a specific angle between steering angles corresponding to the plurality of selected steering images as a steering angle. For example, the ultrasound apparatus 1000 may select a fifth steering image and a sixth steering image each including a medical tool (for example, a needle) having a brightness value greater than a first threshold value and less than a second threshold value from among the plurality of steering images. Also, the ultrasound apparatus 1000 may select a specific steering angle between a fifth steering angle corresponding to the fifth steering image and a sixth steering angle corresponding to the sixth steering image.

For example, the ultrasound apparatus 1000 may select the fifth steering image (for example, a brightness value of the needle in the fifth steering image is 155) and the sixth steering image (for example, a brightness value of the needle in the sixth steering image is 190) each including the needle 30 having a brightness value greater than the first threshold value (for example, 150) and less than the second threshold value (for example, 200) from among the plurality of steering images. Also, the ultrasound apparatus 1000 may determine a specific angle (for example, about 30 degrees) between the fifth steering angle (for example, about 25 degrees) corresponding to the fifth steering image and the sixth steering angle (for example, about 35 degrees) corresponding to the sixth steering image as a steering angle.

In operation S350, the ultrasound apparatus 1000 may obtain a needle ultrasound image by using the detected steering angle.

According to an embodiment, the needle ultrasound image may be an image that combines a steering image generated at the detected steering angle with an SCI. For example, the ultrasound apparatus 1000 may generate a steering image generated at the detected steering angle and an SCI, and generate a needle ultrasound image by overlapping a predetermined portion of the steering image above the SCI. In this case, the predetermined portion of the steering image may be a region of a predetermined size including the needle 30.

According to an embodiment, the ultrasound apparatus 1000 may generate an SCI and a steering image in turns by using the first beamformer and the second beamformer.

Meanwhile, according to an embodiment, the needle ultrasound image may be a steering image itself generated at the detected steering angle. For example, the ultrasound apparatus 1000 may transmit an ultrasound signal of the detected steering angle to an object. Also, the ultrasound apparatus 1000 may obtain a steering image as a needle ultrasound image by using an ultrasound echo signal reflected by the object.

According to an embodiment, in the case where the needle 30 having a brightness value equal to or greater than a threshold value is detected from an SCI, the SCI may be a needle ultrasound image.

In operation S360, the ultrasound apparatus 1000 may display the obtained needle ultrasound image.

According to an embodiment, the ultrasound apparatus 1000 may display the needle ultrasound image on one display and may display the needle ultrasound image on a plurality of displays. For example, the ultrasound apparatus 1000 may display the needle ultrasound image on only a main monitor, and may display the needle ultrasound image on both the main monitor and a control panel.

According to an embodiment, the ultrasound apparatus 1000 may update the needle ultrasound image by a predetermined period. For example, the ultrasound apparatus 1000 may update the needle ultrasound image by transmitting an ultrasound signal every 0.0001 seconds at a detected steering angle and obtaining a real-time steering image.

In this case, a user may recognize the angle and location of the needle inserted into an object in real-time via a needle ultrasound image displayed on the display of the ultrasound apparatus 1000.

Meanwhile, after a time elapses, in the case where the outline of the needle does not accurately appear in the needle ultrasound image due to the movement, etc. of the probe 20, the ultrasound apparatus 1000 may detect a new steering angle. An operation of detecting, at the ultrasound apparatus 1000, the new steering angle is described below in detail with reference to FIG. 12. Hereinafter, an operation of providing, at the ultrasound apparatus 1000, a needle ultrasound image is described below in more detail with reference to FIGS. 4 to 6.

Figure 4:
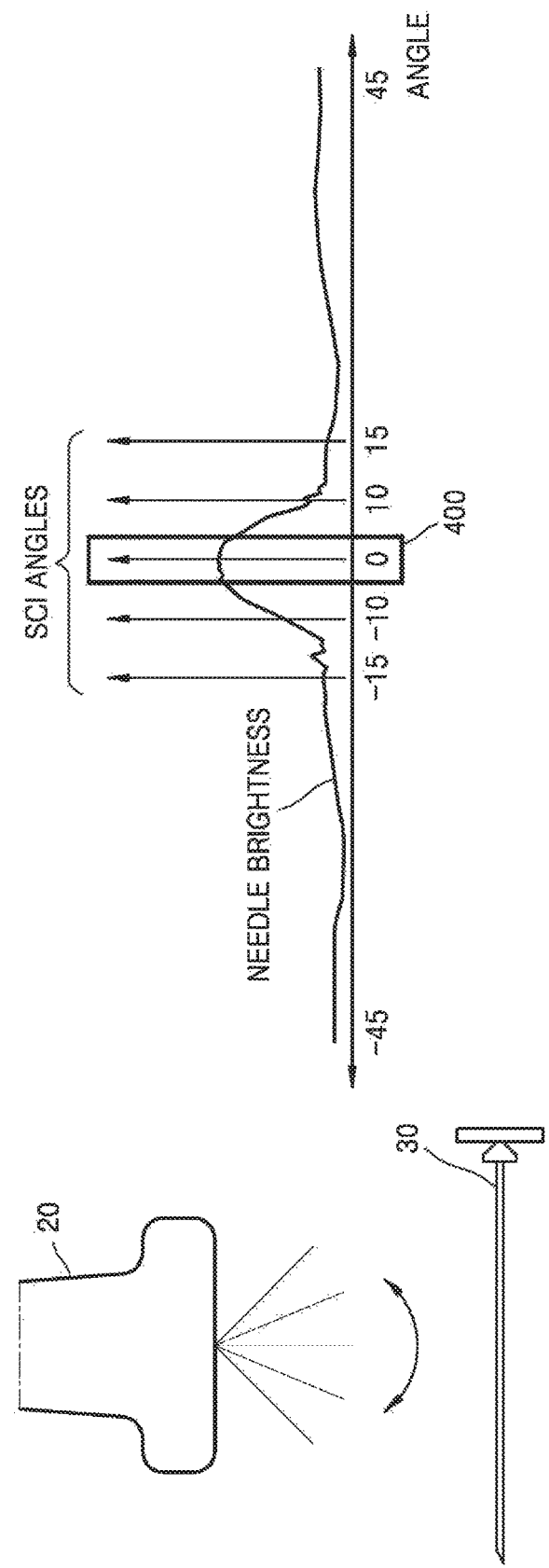
FIG. 4 is a diagram for explaining an operation of detecting, at an ultrasound apparatus, a steering angle when an incident angle of a needle is 0 degree according to an embodiment.

FIG. 4 is a diagram for explaining an operation of detecting, at an ultrasound apparatus, a steering angle in the case where an incident angle of a needle is 0 degree according to an embodiment.

In FIG. 4, a case where the probe 20 is located in parallel to the surface of an object, and the needle 30 is inserted at an incident angle of about 0 degree with respect to the surface of the object is described as an example.

The ultrasound apparatus 1000 may detect a specific steering angle for obtaining a steering image in which the needle 30 has a brightness value greater than a threshold value. For example, the ultrasound apparatus 1000 may obtain steering images (referred to as SCI steering images, hereinafter) corresponding to a plurality of steering angles (referred to as SCI angles, hereinafter, for example, −15 degrees, −10 degrees, 0 degree, 10 degrees, and 15 degrees) for obtaining an SCI.

When a steering angle is 0 degree, since an ultrasound signal is vertically incident to the needle 30, the intensity of an ultrasound echo signal reflected by the needle 30 may be highest. Therefore, the ultrasound apparatus 1000 may detect 0 degree from among SCI angles as a specific steering angle since the brightness value of the needle 30 in a steering image when a steering angle is 0 degree is highest.

Since the ultrasound apparatus 1000 has detected one steering angle (that is, 0 degree) from among the SCI angles (for example, −15 degrees, −10 degrees, 0 degree, 10 degrees, and 15 degrees) as a specific steering angle, the ultrasound apparatus 1000 may not obtain steering images corresponding to other steering angles besides the SCI angles (for example, −15 degrees, −10 degrees, 0 degree, 10 degrees, and 15 degrees).

Meanwhile, the ultrasound apparatus 1000 may display, in real-time, a needle ultrasound image showing the location and angle of the needle 30 on a screen by periodically transmitting an ultrasound signal to an object at a steering angle of '0 degree'.

Figure 5:
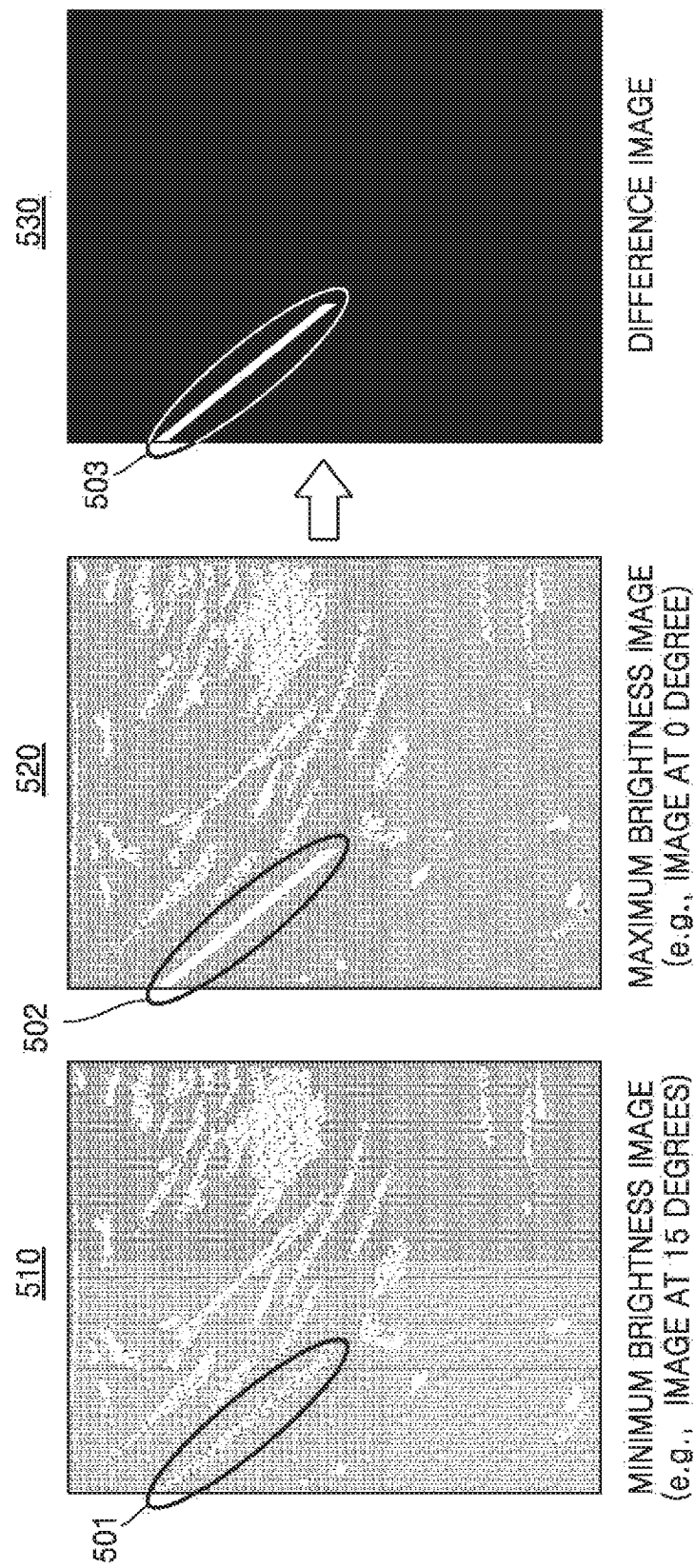
FIG. 5 is a diagram for explaining an operation of detecting, at an ultrasound apparatus, a regular reflection edge by using a difference image between a minimum brightness image and a maximum brightness image according to an embodiment.

FIG. 5 is a diagram for explaining an operation of detecting, at an ultrasound apparatus, a regular reflection edge by using a difference image between a minimum brightness image and a maximum brightness image according to an embodiment.

Referring to FIG. 5, the ultrasound apparatus 1000 may obtain SCI steering images respectively corresponding to SCI angles (for example, −15 degrees, −10 degrees, 0 degree, 10 degrees, and 15 degrees). Also, the ultrasound apparatus 1000 may detect the outline of the needle 30 from each of the SCI steering images by using an outline detection algorithm. For example, the ultrasound apparatus 1000 may detect a region in which the needle 30 is located from each of the SCI steering images by using a characteristic that the needle 30 has a linear form and a characteristic that a brightness value of the needle 30 changes depending on a steering angle.

In this case, the ultrasound apparatus 1000 may select a minimum brightness image 510 in which the needle 30 has a lowest brightness value (for example, a first SCI steering image obtained at a steering angle of 15 degrees) and a maximum brightness image 520 in which the needle 30 has a highest brightness value (for example, a second SCI steering image obtained at a steering angle of 0 degree) from among the SCI steering images. Also, the ultrasound apparatus 1000 may obtain a difference image 530 between the minimum brightness image 510 (the first SCI steering image) and the maximum brightness image 520 (the second SCI steering image). Comparison of the minimum brightness image 510 with the maximum brightness image 520 shows that since a difference in a brightness value appears in only a region (for example, 501 and 502) at which the needle 30 is located and a difference in a brightness value does not appear in the rest of regions, only a region 503 at which the needle 30 is located may appear bright in the difference image 530.

The ultrasound apparatus 1000 may verify whether the needle 30 has been accurately detected from each of the SCI steering images by comparing the region 503 at which the detected needle 30 is located in the difference image 530 with a region at which the needle 30 is located in each of the SCI steering images.

Figure 6:
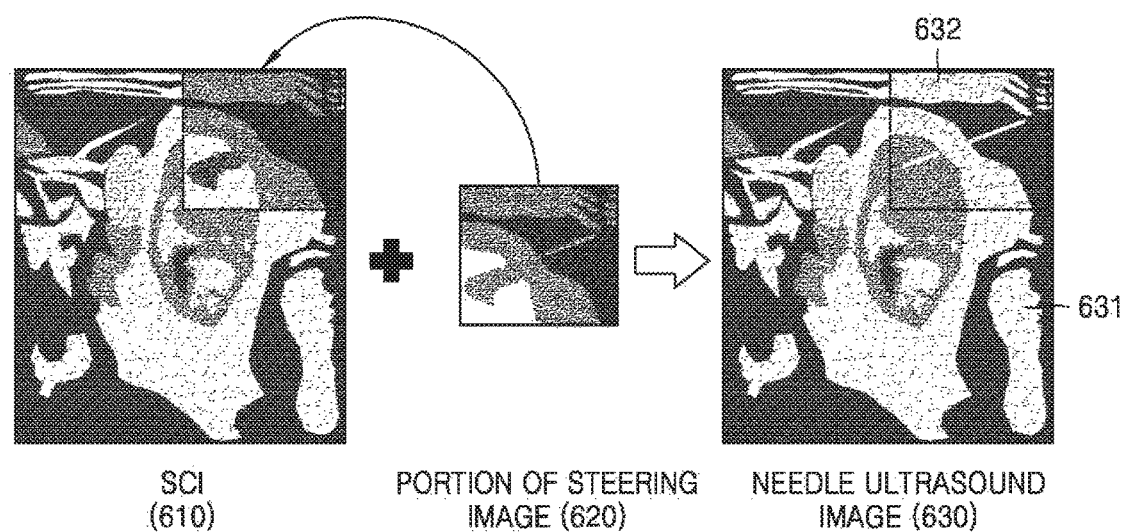
FIG. 6 is a diagram for explaining a needle ultrasound image according to an embodiment.

FIG. 6 is a diagram for explaining a needle ultrasound image according to an embodiment.

Referring to FIG. 6, the ultrasound apparatus 1000 may obtain SCI steering images corresponding to SCI angles (for example, −15 degrees, −10 degrees, 0 degree, 10 degrees, and 15 degrees). Also, the ultrasound apparatus 1000 may generate an SCI 610 by using the SCI steering images, and display the SCI 610 on a screen.

Also, the ultrasound apparatus 1000 may detect a steering angle at which the brightness value of the needle 30 is greater than a threshold value, and obtain a steering image by using the detected steering angle. In this case, the needle 30 may be clearly displayed in the steering image.

The ultrasound apparatus 1000 may display a needle ultrasound image 630 by overlapping a portion 620 of the steering image on a relevant location (for example, a region in which the needle 30 appears) of the SCI 610. In this case, a user may accurately recognize an ultrasound image of a tissue and blood flow by using an SCI region 631 in the needle ultrasound image 630, and clearly recognize the location and direction of the needle 30 by using a steering image region 632.

Hereinafter, for convenience of description, the overlapping of the portion 620 of the steering image on the relevant location (for example, the region in which the needle 30 appears) of the SCI 610 may be expressed by overlapping the steering image above the SCI 610.

Figure 7:
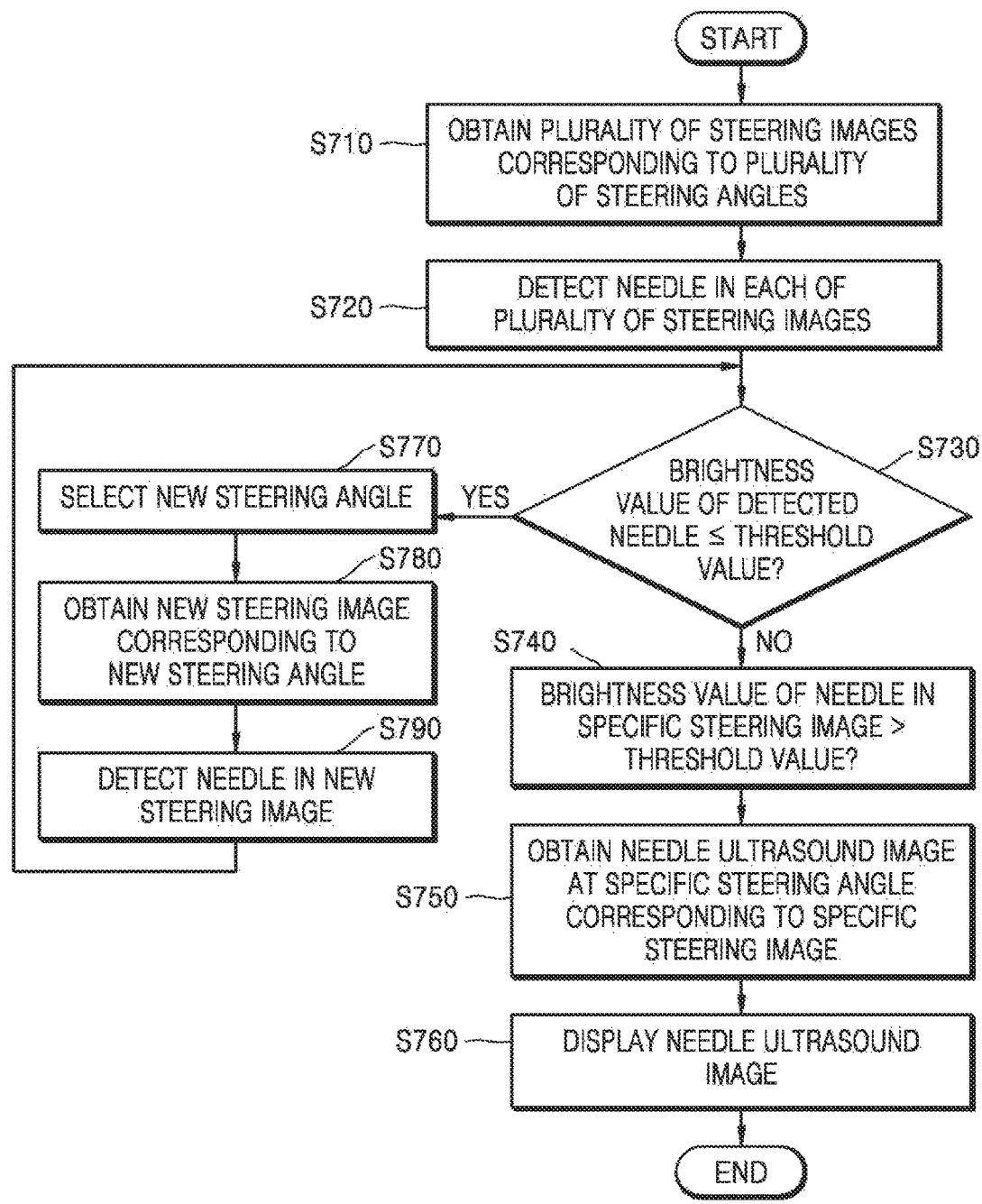
FIG. 7 is a flowchart of explaining a method of providing a needle ultrasound image via an ultrasound apparatus according to an embodiment.

FIG. 7 is a flowchart for explaining a method of providing a needle ultrasound image of an ultrasound apparatus according to an embodiment.

In operation S710, the ultrasound apparatus 1000 may obtain a plurality of steering images corresponding to a plurality of steering angles.

In operation S720, the ultrasound apparatus 1000 may detect the needle in each of the plurality of steering images.

Since operations S710 and S720 respectively correspond to operations S310 and S320 of FIG. 3, descriptions thereof are omitted.

In operation S730, the ultrasound apparatus 1000 may determine whether the brightness value of the needle detected from each of the plurality of steering images is equal to or less than a threshold value. The threshold value may be defined by a user or the system. Also, the threshold value may be a specific value and may be a predetermined range.

In operations S740 and S750, when the brightness value of the needle in a specific steering image from among the plurality of steering images is greater than the threshold value, the ultrasound apparatus 1000 may detect a specific steering angle corresponding to the specific steering image, and obtain a needle ultrasound image by using the specific steering angle. Since the method of obtaining, at the ultrasound apparatus 1000, a needle ultrasound image by using a specific steering angle has been described with reference to FIG. 3, description thereof is omitted.

Meanwhile, in the case where the brightness value of the needle in a first steering image, a second steering image, and a third steering image from among the plurality of steering images is greater than the threshold value, the ultrasound apparatus 1000 may select the first steering image including the needle having a highest brightness value from among the first steering image, the second steering image, and the third steering image. Also, the ultrasound apparatus 1000 may obtain a needle ultrasound image by using a first steering angle corresponding to the selected first steering image.

In operation S760, the ultrasound apparatus 1000 may display the needle ultrasound image on a screen. Since operation S760 corresponds to operation S360 of FIG. 3, description thereof is omitted.

In operation S770, when all of the brightness values of the needle detected from the plurality of steering images are equal to or less than the threshold value, the ultrasound apparatus 1000 may select a new steering angle.

For example, when the brightness values of the needle detected from the first steering image corresponding to the first steering angle and the second steering image corresponding to the second steering angle are equal to or less than the threshold value, the ultrasound apparatus 1000 may select a new third steering angle.

In operation S780, the ultrasound apparatus 1000 may obtain a new steering image corresponding to the new steering angle.

For example, in the case where the new third steering angle is about 30 degrees, the ultrasound apparatus 1000 may generate a third steering image corresponding to the third steering angle (that is, about 30 degrees) by transmitting an ultrasound signal to an object at a steering angle of about 30 degrees, and receiving an ultrasound echo signal from the object.

In operation S790, the ultrasound apparatus 1000 may detect the needle 30 in the new steering image. For example, the ultrasound apparatus 1000 may detect the outline of the needle 30 in the new steering image by using an outline detection algorithm.

In this case, in operation S730, the ultrasound apparatus 1000 may determine whether the brightness value of the needle 30 detected from the new steering image is equal to or less than the threshold value. If the brightness value of the needle 30 detected from the new steering image is equal to or less than the threshold value, the ultrasound apparatus 1000 may select a new steering angle again. In contrast, if the brightness value of the needle 30 detected from the new steering image is greater than the threshold value (operation S740), the ultrasound apparatus 1000 may obtain a needle ultrasound image by using a steering angle corresponding to the new steering image, and display the same (operations S750 and 760).

Meanwhile, in operations S770 and 780, the ultrasound apparatus 1000 may obtain a plurality of new steering images corresponding to a plurality of new steering angles. In this case, when the brightness values of the needle 30 detected from at least two new steering images from among the plurality of new steering images are greater than the threshold value, the ultrasound apparatus 1000 may select a steering image including the needle 30 having a highest brightness value from among the at least two new steering images. Also, the ultrasound apparatus 1000 may obtain and display a needle ultrasound image by using a steering angle of the selected steering image.

An operation of searching for, at the ultrasound apparatus 1000, a steering angle at which the brightness value of the needle 30 is greater than the threshold value from SCI angles first, and when the steering angle at which the brightness value of the needle 30 is greater than the threshold value does not exist among the SCI angles, additionally searching for other steering angles besides the SCI angles is described below with reference to FIG. 8.

FIG. 8 is a diagram for explaining an operation of detecting, at an ultrasound apparatus, a steering angle in the case where an incident angle of a needle is 45 degrees.

In FIG. 8, a case where the probe 20 is located in parallel to the surface of an object, and the needle 30 is inserted at an incident angle of about 45 degrees from the surface of the object is described as an example.

Referring to 810 of FIG. 8, the ultrasound apparatus 1000 may obtain SCI steering images corresponding to SCI angles. For example, the ultrasound apparatus 1000 may generate SCI steering images by transmitting an ultrasound signal to an object at steering angles of −15 degrees, −10 degrees, 0 degree, 10 degrees, and 15 degrees, and receiving an ultrasound echo signal from the object.

In this case, when the ultrasound apparatus 1000 transmits an ultrasound signal to an object by using each of the SCI angles as a steering angle, since an ultrasound signal is not vertically incident to the needle 30, the intensity of an ultrasound echo signal of the needle 30 is low. Therefore, since the brightness value of the needle 30 detected from each of the SCI steering images is equal to or less than the threshold value, the ultrasound apparatus 1000 may search for other steering angles besides the SCI angles.

For example, referring to 820 of FIG. 8, the ultrasound apparatus 1000 may generate first steering images by transmitting an ultrasound signal to an object at a steering angle of about 20 degrees, and receiving an ultrasound echo signal from the object. In this case, the brightness value of the needle 30 in the first steering image is equal to or less than the threshold value. In this case, the ultrasound apparatus 1000 may generate a second steering image corresponding to about 35 degrees by transmitting an ultrasound signal to the object at a steering angle of about 35 degrees instead of about 20 degrees. The brightness value of the needle 30 in the second steering image may be also equal to or less than the threshold value. In this case, the ultrasound apparatus 1000 may generate a third steering image by transmitting an ultrasound signal to the object at a steering angle of about 45 degrees instead of about 35 degrees, and receiving an ultrasound echo signal from the object.

In the case where the ultrasound apparatus 1000 transmits an ultrasound signal at a steering angle of about 45 degrees, since the ultrasound signal is vertically incident to the needle 30, an ultrasound echo signal may be regularly reflected by the needle 30. Therefore, since the brightness value of the needle 30 in the third steering image corresponding to about 45 degrees is greater than the threshold value, the ultrasound apparatus 1000 may generate and display a needle ultrasound image in real-time by using a steering angle of about '45 degrees'.

Figure 9:
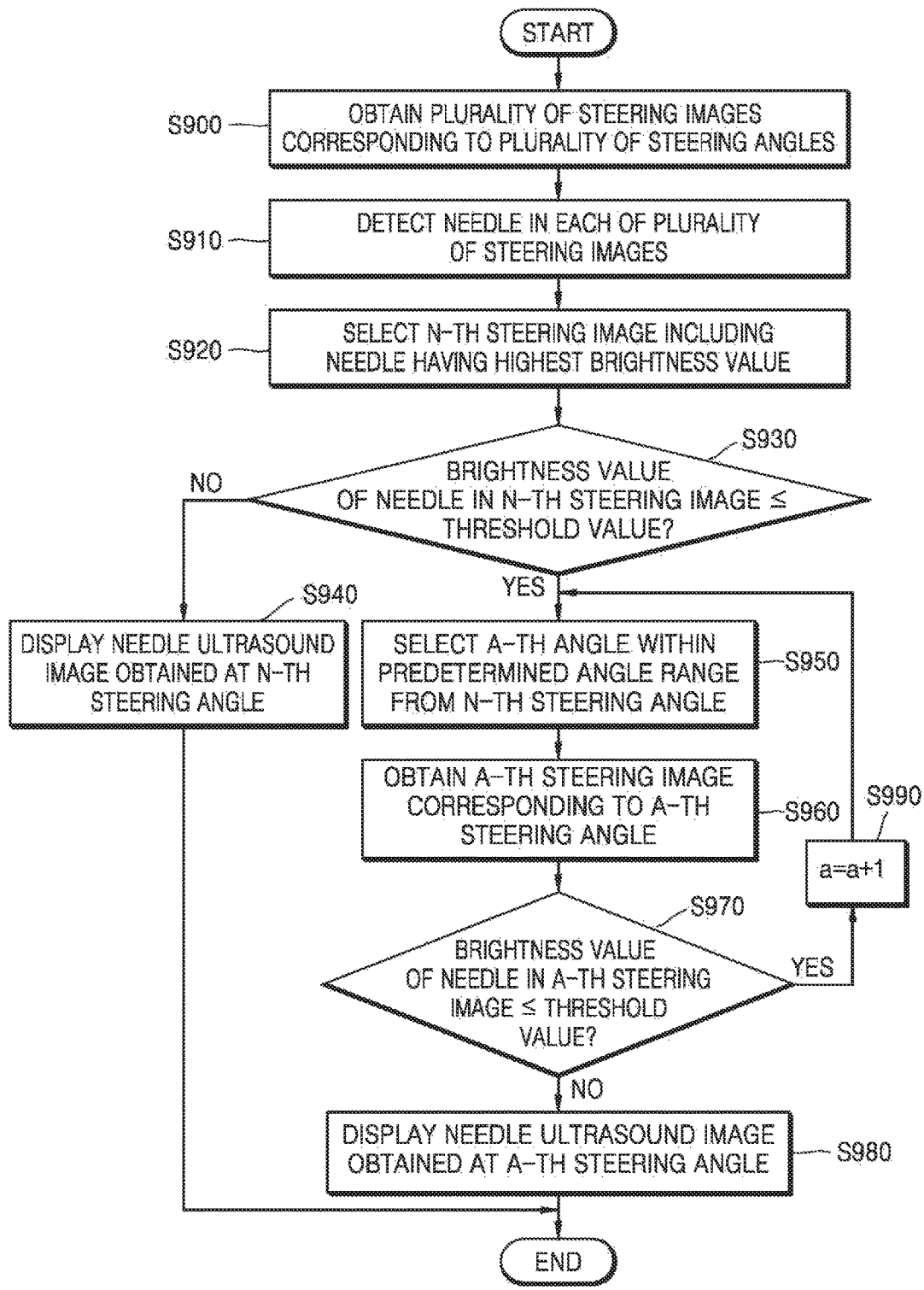
FIG. 9 is a flowchart of a method of providing a needle ultrasound image via an ultrasound apparatus according to an embodiment.

FIG. 9 is a flowchart for explaining a method of providing a needle ultrasound image of an ultrasound apparatus according to an embodiment.

In operation S900, the ultrasound apparatus 1000 may obtain a plurality of steering images corresponding to a plurality of steering angles.

In operation S910, the ultrasound apparatus 1000 may detect a needle in each of the plurality of steering images.

Since operations S900 and S910 correspond to operations S310 and S320 of FIG. 3, descriptions thereof are omitted.

In operation S920, the ultrasound apparatus 1000 may select an n-th steering image including the needle 30 having a highest brightness value from among the plurality of steering images.

In operation S930, the ultrasound apparatus 1000 may determine whether the brightness value of the needle 30 in the n-th steering image is equal to or less than the threshold value. The threshold value may be defined in advance by a user or the system.

In operation S940, when the brightness value of the needle 30 in the n-th steering image is greater than the threshold value, the ultrasound apparatus 1000 may display a needle ultrasound image obtained by using an n-th steering angle corresponding to the n-th steering image on a screen. For example, the ultrasound apparatus 1000 may obtain the n-th steering image in real-time by transmitting an ultrasound signal at the n-th steering angle by a predetermined period. In this case, the ultrasound apparatus 1000 may overlap a portion (a partial region including the needle 30) of the n-th steering image obtained in real-time above an SCI.

In operation S950, when the brightness value of the needle 30 in the n-th steering image is equal to or less than the threshold value, the ultrasound apparatus 1000 may select an a-th steering angle within a predetermined angle range from the n-th steering angle. For example, the ultrasound apparatus 1000 may select the a-th steering angle in the neighborhood of the n-th steering angle based on the n-th steering angle.

Here, the predetermined angle range may increase when the n-th steering angle reduces, and may reduce when the n-th steering angle increases. For example, in the case where the n-th steering angle is about 10 degrees, the predetermined angle range may be about ±15 degrees (that is, about −5 to about 25) from about 10 degrees. In contrast, in the case where the n-th transmission angle is about 40 degrees, the predetermined angle range may be about ±5 degrees (that is, about 35 degrees to about 40 degrees) from about 40 degrees.

A fact that the n-th steering angle is large denotes that the incident angle of the needle 30 is large. Due to a characteristic of the regular reflection of the needle 30, when the incident angle of the needle 30 is large, a search range over which the ultrasound apparatus 1000 may search for a steering angle may reduce. The predetermined angle range for searching for a new steering angle is described below in more detail with reference to FIG. 11.

Meanwhile, in operation S950, the ultrasound apparatus 1000 may select the a-th steering angle within the predetermined angle range from the n-th steering angle without comparing the brightness value of the needle 30 in the n-th steering image with the threshold value. For example, the ultrasound apparatus 1000 may select the a-th steering angle in the neighborhood of the n-th steering angle based on the n-th steering angle.

In operation S960, the ultrasound apparatus 1000 may obtain an a-th steering image corresponding to the a-th steering angle. For example, the ultrasound apparatus 1000 may generate the a-th steering image by transmitting an ultrasound signal to an object at the a-th steering angle, and receiving an ultrasound echo signal from the object.

In operation S970, the ultrasound apparatus 1000 may determine whether the brightness value of the needle 30 in the a-th steering image is equal to or less than the threshold value. For example, the ultrasound apparatus 1000 may detect the outline of the needle 30 from the a-th steering image by using an outline detection algorithm, and determine whether the brightness value of the needle 30 is equal to or less than the threshold value.

In operation S980, when the brightness value of the needle 30 in the a-th steering image is greater than the threshold value, the ultrasound apparatus 1000 may display a needle ultrasound image obtained by using the a-th steering angle on a screen. For example, the ultrasound apparatus 1000 may generate the a-steering image by transmitting an ultrasound signal to an object at the a-th steering angle, and receiving an ultrasound echo signal from the object. Also, the ultrasound apparatus 1000 may overlap a portion of the a-th steering image above an SCI of the object. In this case, the portion of the a-th steering image may be a region in which the needle 30 is displayed.

Meanwhile, in operations S950 and S960, the ultrasound apparatus 1000 may obtain a plurality of a-th steering images corresponding to a plurality of a-th steering angles. In this case, when the brightness values of the needle 30 detected from at least two steering images from among the plurality of a-th steering images are greater than the threshold value, the ultrasound apparatus 1000 may select a steering image including the needle 30 having a highest brightness value from among the at least two steering images. Also, the ultrasound apparatus 1000 may obtain and display a needle ultrasound image by using a steering angle of the selected steering image.

In operation S990, when the brightness value of the needle 30 in the a-th steering image is equal to or less than the threshold value, the ultrasound apparatus 1000 may select a new steering angle. For example, the ultrasound apparatus 1000 may select an (a+1)-th steering angle instead of the a-th steering angle. In this case, the ultrasound apparatus 1000 may determine the (a+1)-th steering angle within a predetermined angle range from the a-th steering angle or the n-th steering angle.

The ultrasound apparatus 1000 may detect a specific steering angle at which the needle 30 clearly appears by performing operations S950 to S990 based on the (a+1)-th steering angle.

FIG. 10 is a diagram for explaining an operation of adaptively detecting, at an ultrasound apparatus, a steering angle.

In operation S1010, since the incident angle of the needle 30 is not known, the ultrasound apparatus 1000 may select a plurality of steering angles at a wide interval, and obtain a plurality of steering images corresponding to a plurality of steering angles. For example, the ultrasound apparatus 1000 may obtain steering images respectively corresponding to SCI angles (for example, −15 degrees, −10 degrees, 0 degree, 10 degrees, and 15 degrees), and −45 degrees, −35 degrees, −25 degrees, 25 degrees, 35 degrees, and 45 degrees.

Also, the ultrasound apparatus 1000 may compare brightness values of the needle 30 in the plurality of steering images, and select a first steering image corresponding to about 25 degrees including the needle 30 having a highest brightness value.

In operation S1020, when the brightness value of the needle 30 in the first steering image is equal to or less than the threshold value, the ultrasound apparatus 1000 may search for a new steering angle in the neighborhood of about 25 degrees. For example, the ultrasound apparatus 1000 may select about 27 degrees as a steering angle, and obtain a second steering image corresponding to about 27 degrees. In this case, since the brightness value of the needle 30 in the second steering image is greater than the threshold value, the ultrasound apparatus 1000 may transmit an ultrasound signal at a steering angle of about 27 degrees, and periodically obtain the second steering image corresponding to about 27 degrees. Also, the ultrasound apparatus 1000 may provide a needle ultrasound image in real-time by displaying the second steering image above an SCI.

Figure 11:
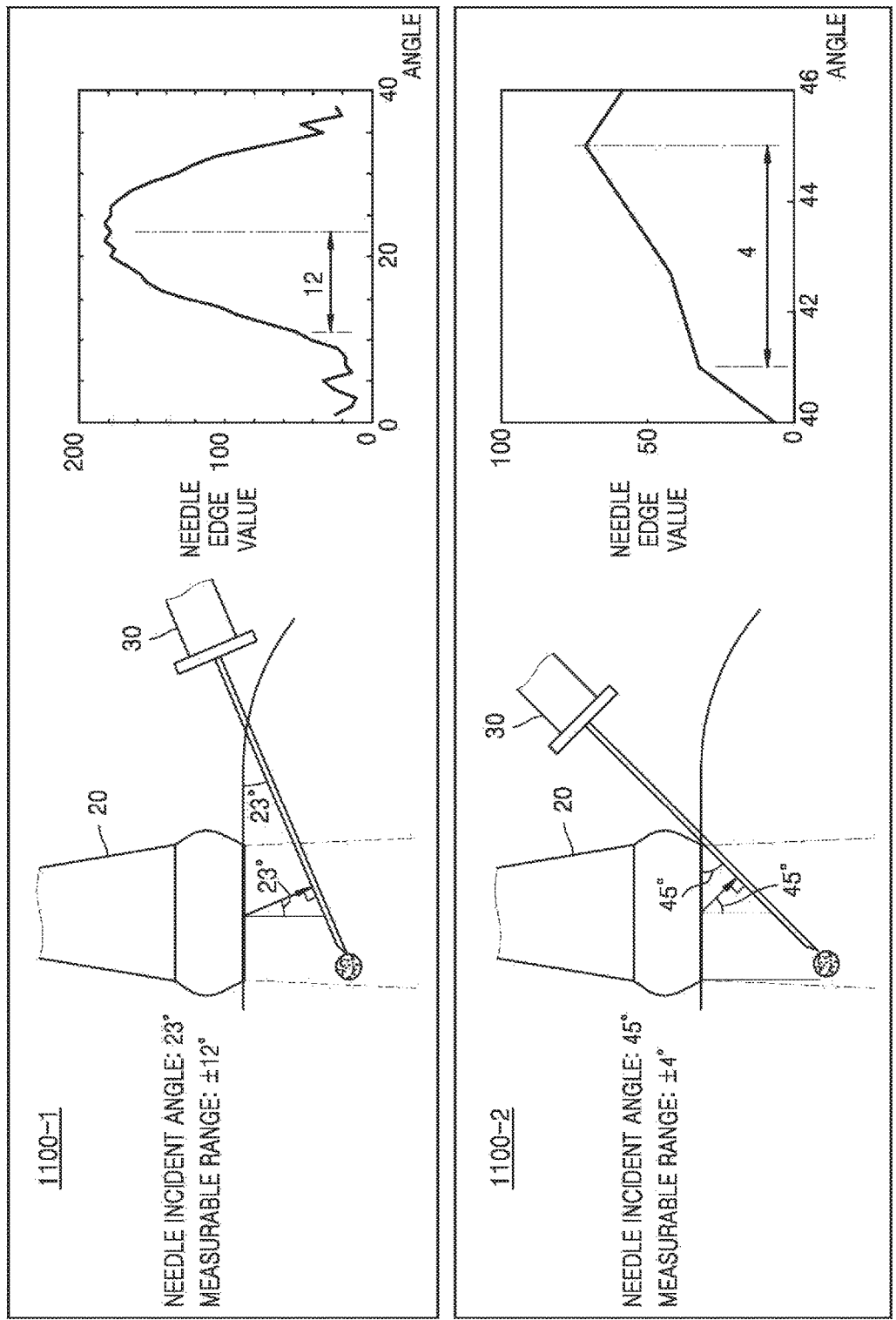
FIG. 11 is a diagram for explaining an operation of defining a search range for detecting, at an ultrasound apparatus, a steering angle.

FIG. 11 is a diagram for explaining an operation of defining a search range for detecting, at an ultrasound apparatus, a steering angle.

Referring to 1100-1, in the case where the probe 20 is located in parallel to the surface of an object, and the needle 30 is inserted at an incident angle of about 23 degrees from the surface of the object, a measurable range in which the brightness value of the needle 30 may be measured may be ±12.

Therefore, in the case where it is expected that the incident angle of the needle 30 is about 23 degrees, the ultrasound apparatus 1000 may determine a predetermined angle range as 'about 23 degrees±12 (that is, about 11 degrees or about 35 degrees)', and search for a steering angle at which the brightness value of the needle 30 is greater than the threshold value between about 11 degrees and about 35 degrees.

Referring to 1100-2, in the case where the probe 20 is located in parallel to the surface of an object, and the needle 30 is inserted at an incident angle of about 40 degrees from the surface of the object, a measurable range in which the brightness value of the needle 30 may be measured may be ±4.

Therefore, in the case where it is expected that the incident angle of the needle 30 is about 45 degrees, the ultrasound apparatus 1000 may determine a predetermined angle range as 'about 45 degrees±4 (that is, about 41 degrees or about 49 degrees)', and search for a steering angle at which the brightness value of the needle 30 is greater than the threshold value between about 41 degrees and about 49 degrees.

Consequently, since a measurable range reduces when the incident angle of the needle 30 is about 45 degrees rather than about 23 degrees, as the incident angle of the needle 30 is large, a search range in which the ultrasound apparatus 1000 may search for a steering angle reduces.

Figure 12:
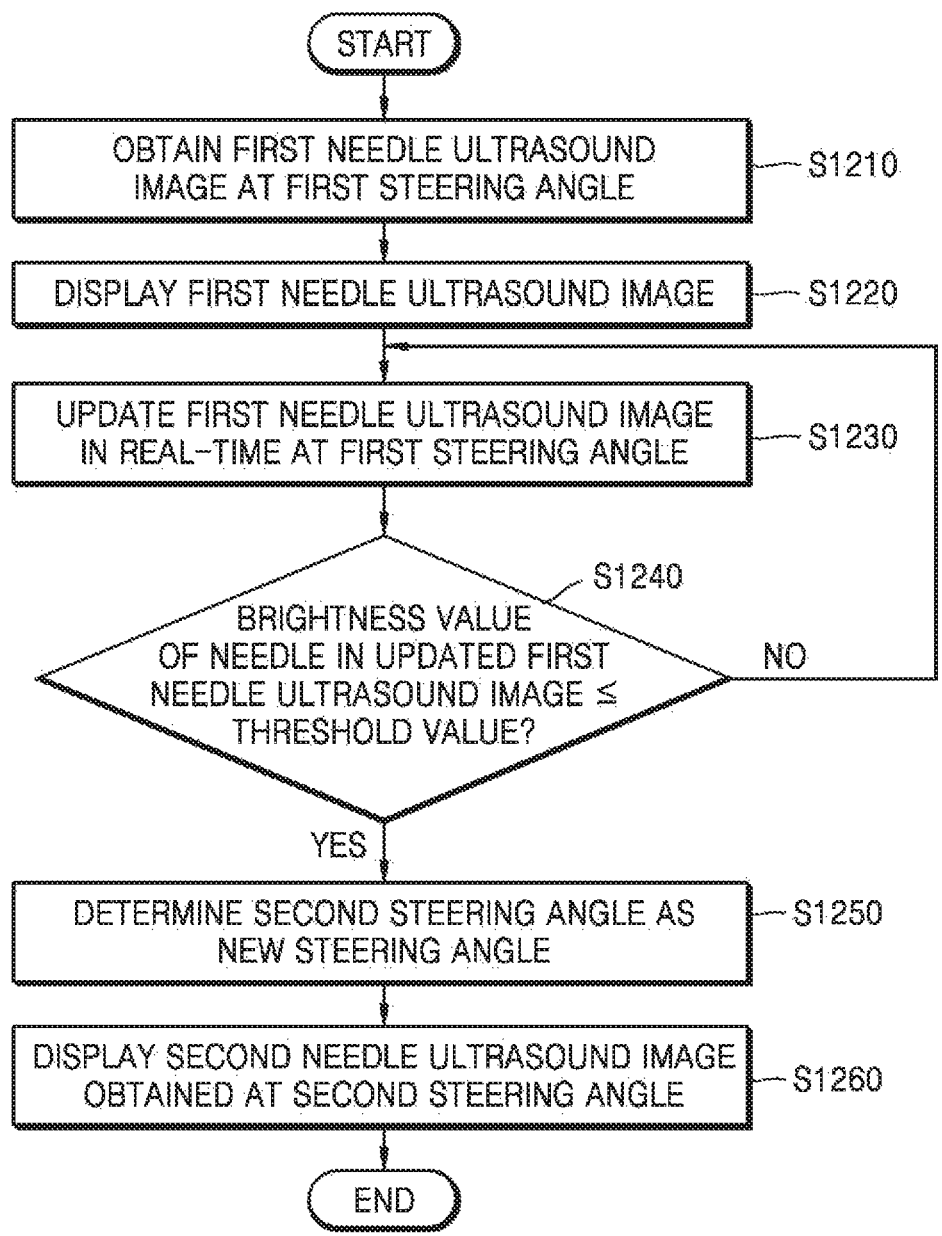
FIG. 12 is a flowchart of a method of providing, at an ultrasound apparatus, a needle ultrasound image updated in real-time according to an embodiment.

FIG. 12 is a flowchart for explaining a method of providing, at an ultrasound apparatus, a needle ultrasound image updated in real-time according to an embodiment.

In operation S1210, the ultrasound apparatus 1000 may obtain a first needle ultrasound image by using a first steering angle.

In operation S1220, the ultrasound apparatus 1000 may display the first needle ultrasound image.

Since operations S1210 and S1220 correspond to operations S350 and S360 of FIG. 3, descriptions thereof are omitted.

In operation S1230, the ultrasound apparatus 1000 may update the first needle ultrasound image in real-time by using the first steering angle. The updating of the first needle ultrasound image in real-time may denote newly obtaining the first needle ultrasound image by transmitting an ultrasound signal at the first steering angle.

For example, the ultrasound apparatus 1000 may obtain the first steering image corresponding to the first steering angle (for example, about 30 degrees) by transmitting an ultrasound signal at the first steering angle (for example, about 30 degrees) to an object for every 0.001 second, and receiving an ultrasound echo signal reflected by the object. Also, the ultrasound apparatus 1000 may update the first needle ultrasound image by overlapping a portion (for example, a region in which the needle 30 is displayed) of the first steering image obtained for every 0.001 second above an SCI.

In operation S1240, the ultrasound apparatus 1000 may determine whether the brightness value of the needle 30 in the updated first needle ultrasound image is equal to or less than the threshold value. For example, the ultrasound apparatus 1000 may monitor whether the brightness value of the needle 30 inside the first needle ultrasound image updated in real-time is equal to or less than the threshold value.

In operation S1250, when the brightness value of the needle 30 in the updated first needle ultrasound image is equal to or less than the threshold value, the ultrasound apparatus 1000 may determine a second steering angle as a new steering angle. The second steering angle may be an angle at which the brightness value of the needle 30 in a second steering image obtained at the second steering angle is greater than the threshold value.

For example, the ultrasound apparatus 1000 may search for the second steering angle within a predetermined angle range from the first steering angle. Also, in the case where the second steering angle is not searched for within the predetermined angle range from the first steering angle, the ultrasound apparatus 1000 may search for the second steering angle over an entire angle range (for example, about −45 degrees to about 45 degrees).

In operation S1260, the ultrasound apparatus 1000 may display a second needle ultrasound image obtained by using the second steering angle on a screen.

For example, the ultrasound apparatus 1000 may obtain the second steering image corresponding to the second steering angle (for example, about 35 degrees) by transmitting an ultrasound signal to an object at the second steering angle (for example, about 35 degrees) for every 0.001 second, and receiving an ultrasound echo signal reflected by the object. Also, the ultrasound apparatus 1000 may provide the second needle ultrasound image by overlapping a portion (for example, a region in which the needle 30 is displayed) of the second steering image obtained for every 0.001 second above an SCI.

Figure 13:
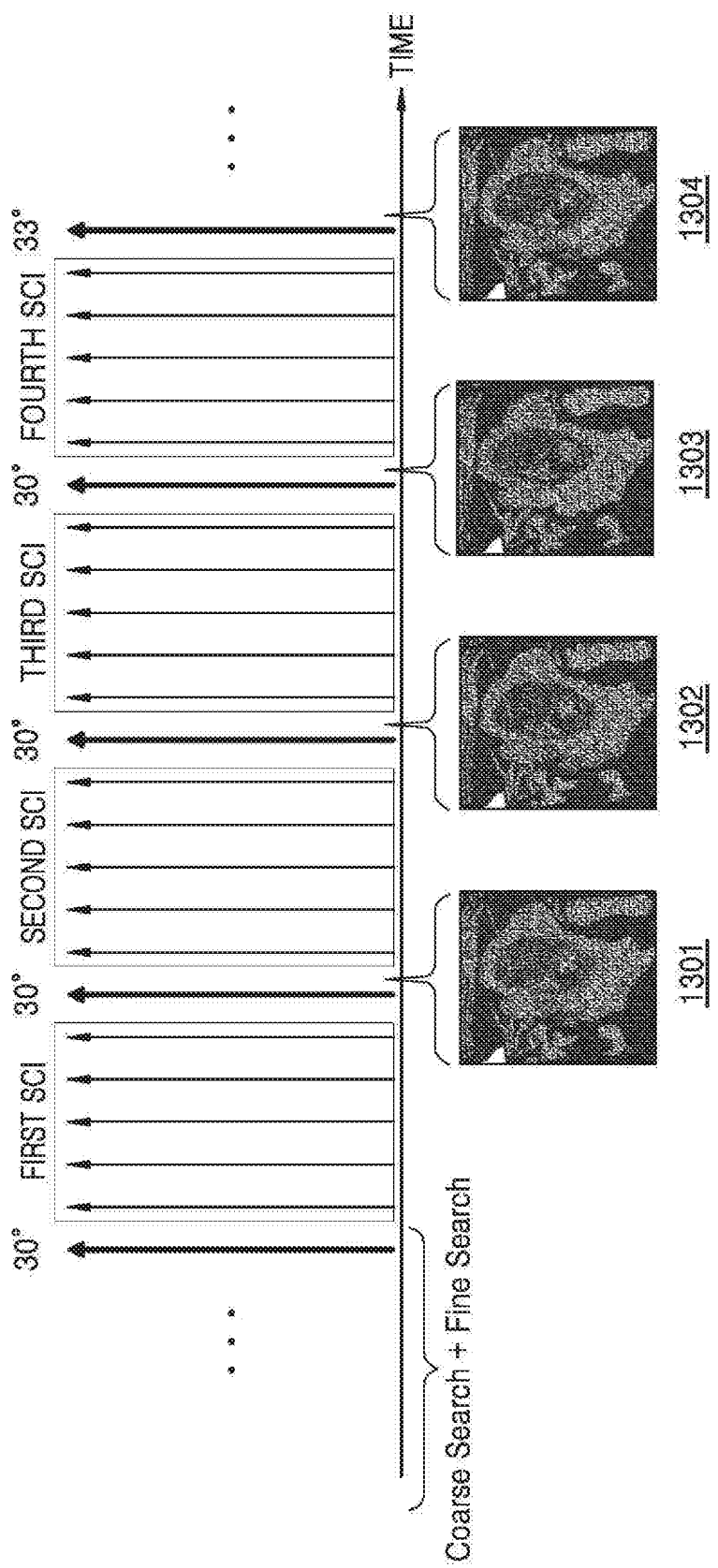
FIG. 13 is a diagram for explaining a method of detecting, at an ultrasound apparatus, a steering angle according to an embodiment.

FIG. 13 is a diagram for explaining a method of detecting, at an ultrasound apparatus, a steering angle according to an embodiment.

Referring to FIG. 13, the ultrasound apparatus 1000 may detect 'about 30 degrees', which is a steering angle clearly showing the needle 30, via each operation of FIG. 10. In this case, the ultrasound apparatus 1000 may display a needle ultrasound image in real-time by generating and overlapping an SCI and a steering image.

For example, the ultrasound apparatus 1000 may generate a first SCI by using SCI steering images. After that, the ultrasound apparatus 1000 may obtain a first steering image corresponding to a steering angle of about 30 degrees, and display a first needle ultrasound image 1301 by overlapping a portion of the first steering image above the first SCI.

Next (for example, after 0.0001 second), the ultrasound apparatus 1000 may generate a second SCI by using SCI steering images. Also, the ultrasound apparatus 1000 may obtain a first steering image corresponding to a steering angle of about 30 degrees, and display a second needle ultrasound image 1302 by overlapping a portion of the first steering image above the second SCI.

The ultrasound apparatus 1000 may generate a third SCI by using SCI steering images. Also, the ultrasound apparatus 1000 may obtain a first steering image corresponding to a steering angle of about 30 degrees, and display a third needle ultrasound image 1303 by overlapping a portion of the first steering image above the third SCI.

In this case, since the needle 30 does not clearly appear in the third needle ultrasound image 1303 (for example, the brightness value of the needle 30 is equal to or less than the threshold value), the ultrasound apparatus 1000 may select a new steering angle (for example, about 33 degrees) instead of about 30 degrees.

For example, the ultrasound apparatus 1000 may generate a fourth SCI by using SCI steering images. Also, the ultrasound apparatus 1000 may obtain a second steering image corresponding to the newly selected steering angle of about 33 degrees instead of about 30 degrees, and display a fourth needle ultrasound image 1304 by overlapping a portion of the second steering image above the fourth SCI.

Therefore, according to an embodiment, the ultrasound apparatus 1000 may perform in turns the generating of an SCI and the detecting of a steering angle at which the brightness value of the needle 30 is equal to or greater than the threshold value.

Figure 14:
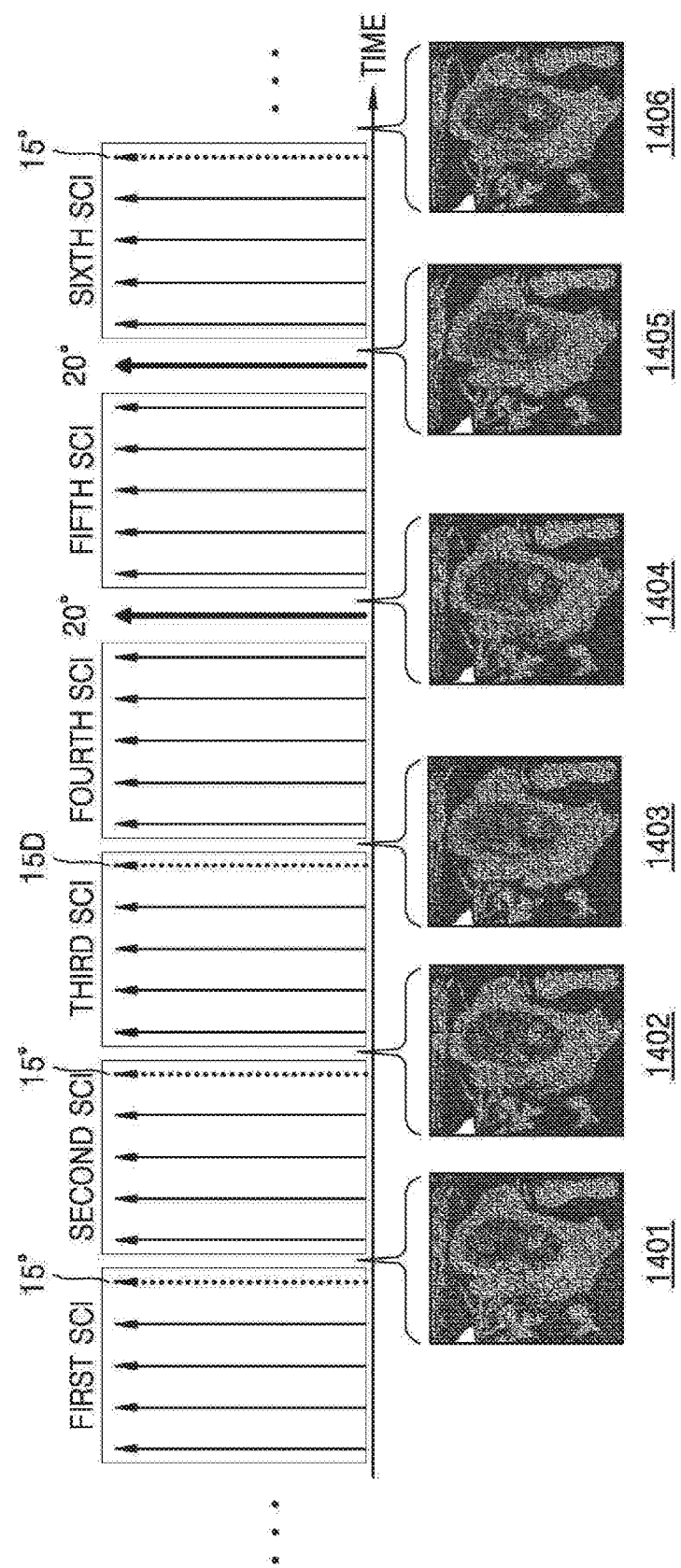
FIG. 14 is a diagram for explaining an operation of displaying, at an ultrasound apparatus, a needle ultrasound image by using a steering angle defined in advance and used for obtaining a spatial compound image.

FIG. 14 is a diagram for explaining an operation of displaying, at an ultrasound apparatus, a needle ultrasound image by using a steering angle defined in advance used for obtaining an SCI.

In FIG. 14, a case where the ultrasound apparatus 1000 has detected 'about 15 degrees', which is one of SCI angles (for example, −15 degrees, −10 degrees, 0 degree, 10 degrees, and 15 degrees), as a steering angle at which the needle 30 clearly appears is described an as example.

The ultrasound apparatus 1000 may generate a first SCI by compounding SCI steering images corresponding to SCI angles. In this case, since the brightness value of the needle 30 detected from a first SCI steering image corresponding to a steering angle of about 15 degrees from among the SCI steering images is greater than the threshold value, the ultrasound apparatus 1000 may display a first needle ultrasound image 1401 by overlapping a portion of the first SCI steering image in which the needle 30 appears above the first SCI.

Also, after a predetermined time elapses (for example, after 0.0001 second), the ultrasound apparatus 1000 may generate a second SCI by compounding SCI steering images corresponding to SCI angles. In this case, the ultrasound apparatus 1000 may select a portion in which the needle 30 appears from the first SCI steering image corresponding to a steering angle of about 15 degrees, and display a second needle ultrasound image 1402 by overlapping the selected portion above the second SCI.

Also, after a predetermined time elapses (for example, after 0.0001 second), the ultrasound apparatus 1000 may generate a second SCI by compounding SCI steering images corresponding to SCI angles. In this case, the ultrasound apparatus 1000 may display a third needle ultrasound image 1403 by overlapping a portion in which the needle 30 appears from among the first SCI steering image corresponding to a steering angle of about 15 degrees above the third SCI.

However, since the brightness value of the needle 30 is equal to or less than the threshold value in the third needle ultrasound image 1403, the ultrasound apparatus 1000 may select a new steering angle (for example, about 20 degrees) instead of about 15 degrees.

For example, the ultrasound apparatus 1000 may generate a fourth SCI by using SCI steering images. Also, the ultrasound apparatus 1000 may obtain a steering image corresponding to the newly selected steering angle of about 20 degrees instead of about 15 degrees, and display a fourth needle ultrasound image 1404 by overlapping a portion of the second steering image above the fourth SCI. In this case, since the brightness value of the needle 30 in the fourth needle ultrasound image 1404 is greater than the threshold value, the ultrasound apparatus 1000 may continue to generate a needle ultrasound image by using the steering angle of about 20 degrees.

For example, the ultrasound apparatus 1000 may generate a fifth SCI by using SCI steering images. Also, the ultrasound apparatus 1000 may obtain the second steering image corresponding to the steering angle of about 20 degrees, and display a fifth needle ultrasound image 1405 by overlapping a portion of the second steering image above the fifth SCI. However, since the brightness value of the needle 30 is equal to or less than the threshold value in the fifth needle ultrasound image 1405, the ultrasound apparatus 1000 may detect a new steering angle instead of about 20 degrees.

For example, the ultrasound apparatus 1000 may generate a sixth SCI by using SCI steering images. In this case, when the brightness value of the needle 30 detected from the first SCI steering image corresponding to the steering angle of about 15 degrees from among the SCI steering images is greater than the threshold value, the ultrasound apparatus 1000 may display a sixth needle ultrasound image 1406 by overlapping a portion (for example, a region in which the needle 30 is displayed) of the first SCI steering image above the sixth SCI.

That is, according to an embodiment, the ultrasound apparatus 1000 may use one of SCI angles to track the needle 30 inserted into the object.

Figure 15:
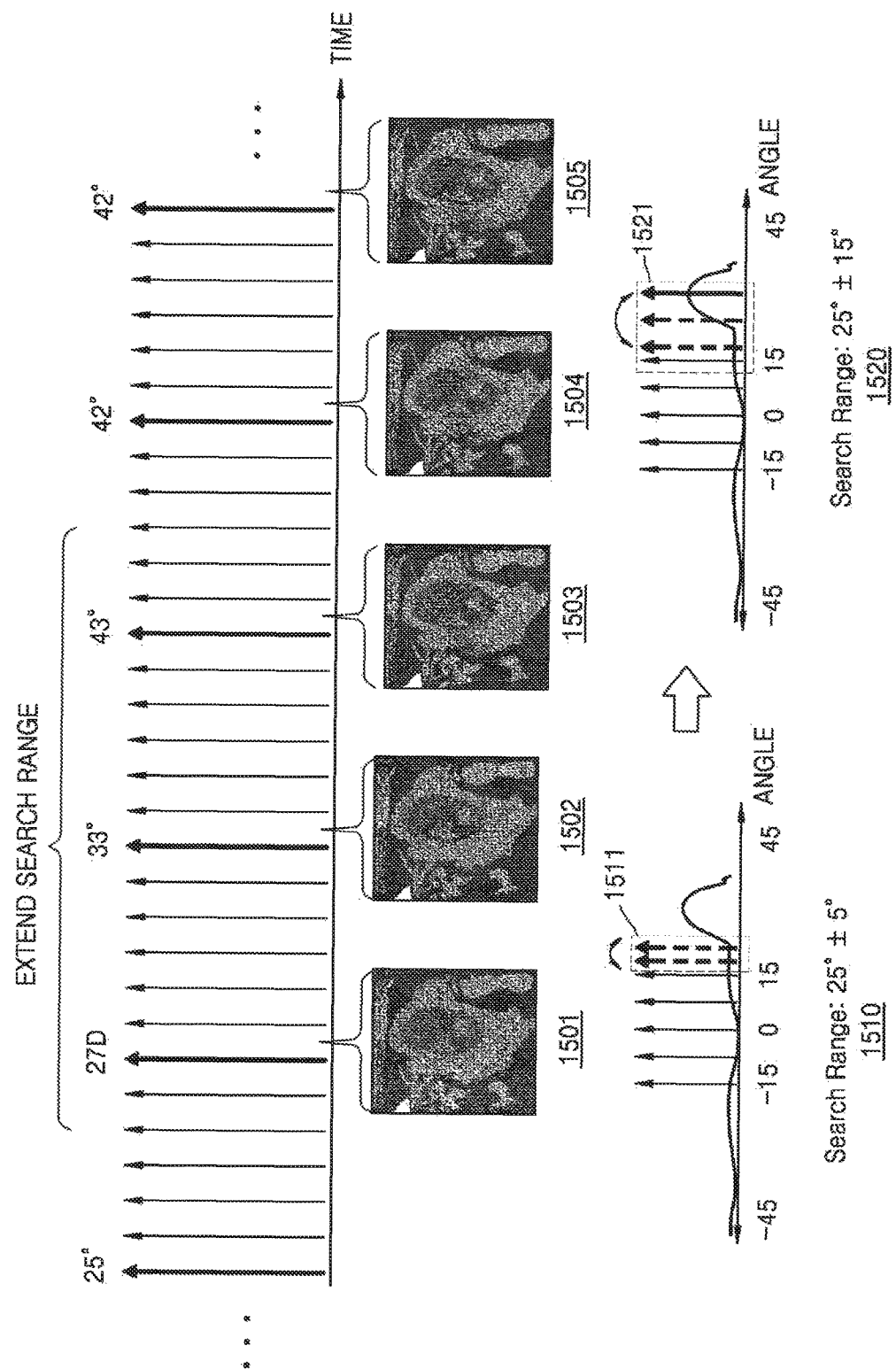
FIG. 15 is a diagram for explaining an operation of extending a search range for detecting, at an ultrasound apparatus, a steering angle according to an embodiment.

FIG. 15 is a diagram for explaining an operation of extending a search range for detecting, at an ultrasound apparatus, a steering angle according to an embodiment.

Referring to FIG. 15, the ultrasound apparatus 1000 may gradually extend a search range used for searching for a predetermined angle. For example, in the case where the needle 30 clearly appears and then disappears in a needle ultrasound image corresponding to a steering angle of about 25 degrees, the ultrasound apparatus 1000 may obtain a needle ultrasound image by using a steering angle in the neighborhood of about 25 degrees in order to obtain a needle ultrasound image in which the needle 30 clearly appears.

For example, the ultrasound apparatus 1000 may set a search range to 'about 25 degrees±5 degrees (1510)', and obtain a first needle ultrasound image 1501 by using a steering angle (for example, about 27 degrees) within the search range. In this case, since the brightness value of the needle 30 in the first needle ultrasound image 1501 is much less than the threshold value, the ultrasound apparatus 1000 may extend the search range further.

For example, the ultrasound apparatus 1000 may set a search range to 'about 25 degrees±10 degrees', and obtain a second needle ultrasound image 1502 by using a steering angle (for example, about 33 degrees) within the search range. In this case, since the brightness value of the needle 30 in the second needle ultrasound image 1502 is much less than the threshold value, the ultrasound apparatus 1000 may extend the search range further.

For example, the ultrasound apparatus 1000 may set a search range to 'about 25 degrees±15 degrees (1520)' again, and obtain a third needle ultrasound image 1503 by using a steering angle (for example, about 43 degrees) within the search range. In this case, since the brightness value of the needle 30 in the third needle ultrasound image 1503 is nearly similar to the threshold value, the ultrasound apparatus 1000 may select a new steering angle in the neighborhood of about 43 degrees.

For example, the ultrasound apparatus 1000 may obtain a fourth needle ultrasound image 1504 by using a steering angle of about 42 degrees. In this case, since the brightness value of the needle 30 in the fourth needle ultrasound image 1504 is greater than the threshold value, the ultrasound apparatus 1000 may continue to update the needle ultrasound image by using the steering angle of about 42 degrees. For example, the ultrasound apparatus 1000 may obtain a fifth needle ultrasound image 1505 corresponding to the steering angle of about 42 degrees.

Figure 16:
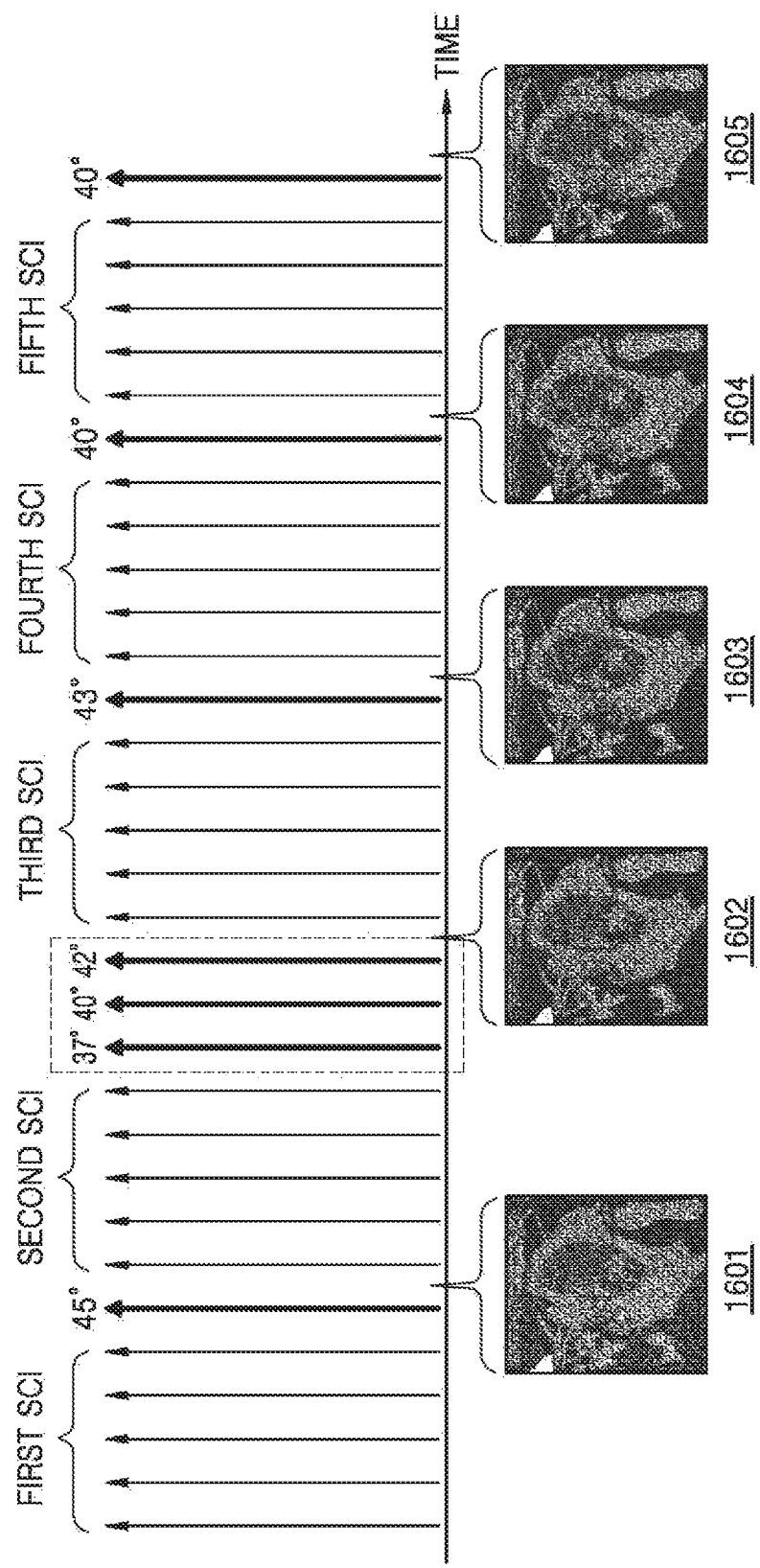
FIG. 16 is a diagram for explaining an operation of detecting a plurality of steering images while an ultrasound apparatus obtains a spatial compound image.

FIG. 16 is a diagram for explaining an operation of detecting a plurality of steering images while an ultrasound apparatus obtains a spatial compound image.

According to an embodiment, the ultrasound apparatus 1000 may obtain an SCI and a steering image in turns, and may obtain an SCI and then obtain a plurality of steering images corresponding to a plurality of steering angles.

For example, the ultrasound apparatus 1000 may obtain a first SCI and obtain a first steering image corresponding to about 45 degrees, and generate a first needle ultrasound image 1601 by overlapping a portion (for example, a region in which the needle 30 is displayed) of the first steering image above the first SCI.

Also, the ultrasound apparatus 1000 may obtain a second SCI, and then obtain a second steering image, a third steering image, and a fourth steering image respectively corresponding to about 37 degrees, about 40 degrees, and about 42 degrees. In this case, the ultrasound apparatus 1000 may select a steering image including the needle 30 having a highest brightness value from among the second steering image, the third steering image, and the fourth steering image, and generate a second needle ultrasound image by overlapping a portion (for example, a region in which the needle 30 is displayed) of the selected steering image above the second SCI.

A frame rate of a second method of generating the second needle ultrasound image 1602 may deteriorate compared with a first method of generating the first needle ultrasound image 1601, but a speed of the second method that detects a steering angle at which the needle 30 clearly appears may be faster than that of the first method.

Meanwhile, according to an embodiment, the ultrasound apparatus 1000 may display an SCI while detecting the needle 30 having a brightness value equal to or greater than the threshold value, and determine a steering angle at which the needle 30 having a brightness value equal to or greater than the threshold value is detected when the brightness value of the needle 30 detected from the SCI is less than the threshold value. In this case, the determined steering angle may be different from SCI angles. Also, the ultrasound apparatus 1000 may display an image (referred to as a 'combined image' hereinafter) that combines a portion of a steering image at the determined steering angle with an SCI on a screen. Also, the ultrasound apparatus 1000 may display the SCI on the screen again when the brightness value of the needle 30 detected from the SCI is equal to or greater than the threshold value while displaying the combined image. That is, the ultrasound apparatus 1000 may display the SCI and the combined image in turns.

In this case, the ultrasound apparatus 1000 may display an indication representing whether an image displayed on the screen is an SCI or a combined image together with the image. An example of an indication representing a kind of an ultrasound image displayed on the screen is described with reference to FIGS. 17 to 20.

FIGS. 17 to 20 are diagrams for explaining an indication representing a kind of an ultrasound image displayed on a screen.

Referring to FIG. 17, the ultrasound apparatus 1000 does not display a separate indicator while an SCI 1710 is displayed on the screen, and may display an indicator 1701 representing that an ultrasound image displayed on the screen is a combined image 1720 in the case where the combined image 1720 (for example, an image that combines an SCI with a steering image at a specific steering angle) is displayed on the screen.

For example, the indicator 1701 may be an icon representing a shape in which an ultrasound beam is steered at a specific angle from the probe 20. In this case, an arrow direction of the icon may change depending on a steering angle corresponding to a steering image combined above an SCI. For example, in the case where a steering angle corresponding to a steering image is about −30 degrees, the arrow may be displayed in the left direction, and in the case where a steering angle corresponding to a steering image is about +20 degrees, the arrow may be displayed in the right direction.

Referring to FIG. 18, the ultrasound apparatus 1000 may display text 'SCI' 1801 representing an SCI 1810 together with the SCI 1810 while the SCI 1810 is displayed on a screen. In this case, the text 'SCI' 1801 may be displayed in a portion on the SCI 1810, and may be displayed in a region that does not overlap the SCI 1810.

In the case where a combined image 1820 (for example, an image that combines an SCI with a steering image at a specific steering angle) is displayed on the screen, the ultrasound apparatus 1000 may display an indicator 1802 representing the ultrasound image displayed on the screen is the combined image 1820. In this case, the indicator 1802 may display a steering angle and a direction corresponding to the steering image combined above the SCI. For example, in the case where a steering image obtained by using a steering angle of about 30 degrees is combined above an SCI, the indicator 1802 may display a 'line to the right direction' and '30°'.

According to an embodiment, the indicator 1802 may be displayed on a portion on the combined image 1820, and may be displayed on a region that does not overlap the combined image 1820. Also, though FIG. 18 explains a case where the indicator 1802 has a fan shape as an example, the indicator 1802 is not limited thereto. For example, the indicator 1802 may have various shapes such as a circle, a quadrangle, a triangle, a protractor, and a compass.

Figure 19:
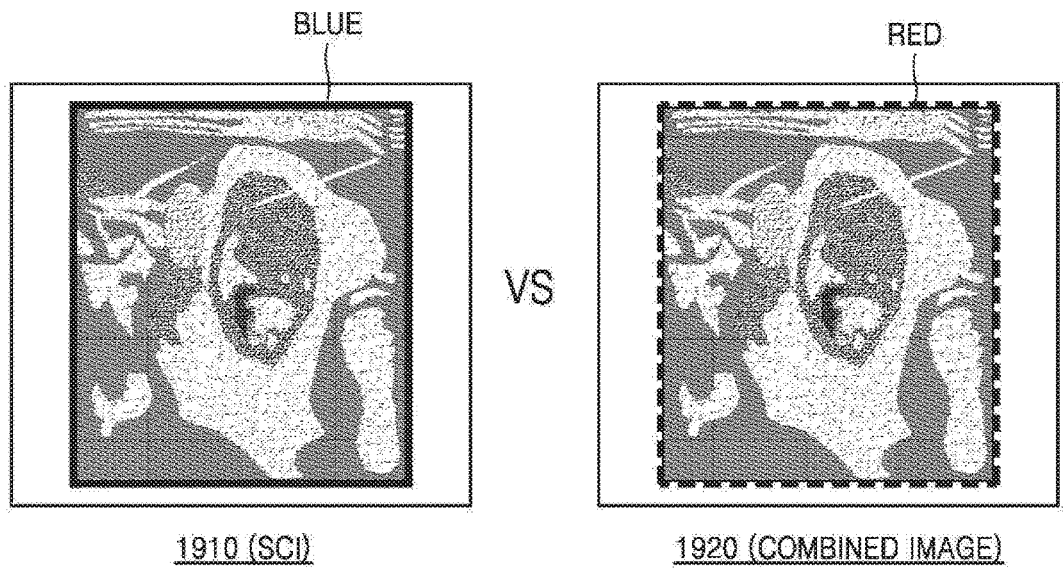

Referring to FIG. 19, the ultrasound apparatus 1000 may display the edge of an image display region by using a first color (for example, blue) while an SCI 1910 is displayed in the image display region, and display the edge of the image display region by using a second color (for example, red) while a combined image 1920 is displayed in the image display region.

According to an embodiment, the ultrasound apparatus 1000 may display the edge of the image display region by using a solid line while the SCI 1910 is displayed in the image display region, and display the edge of the image display region by using a dotted line or an alternated long and short dash line while the combined image 1920 is displayed in the image display region.

Figure 20:
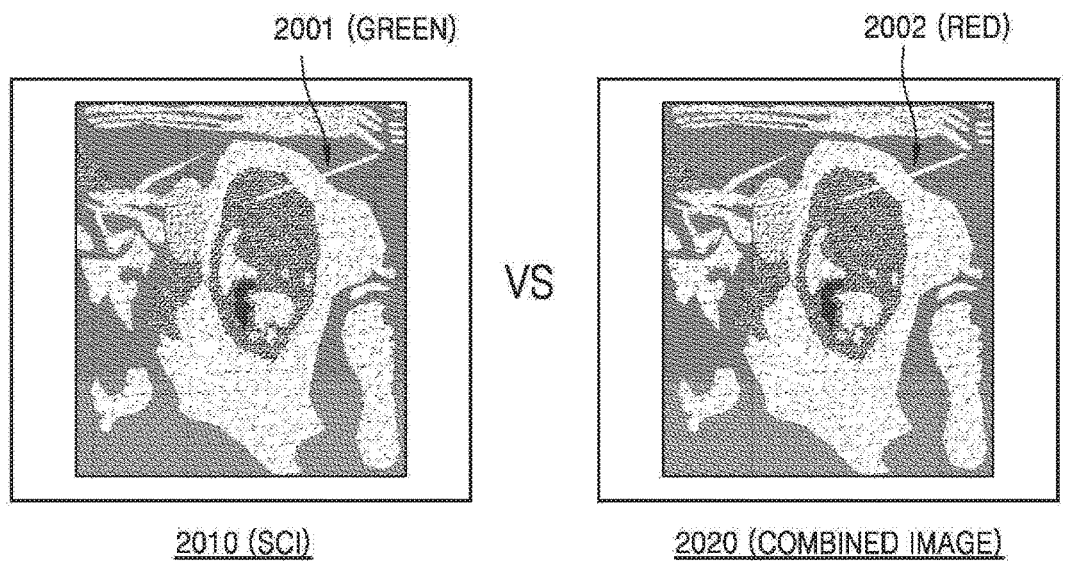

Referring to FIG. 20, the ultrasound apparatus 1000 may display a needle portion 2001 detected from an SCI 2010 by using a first color (for example, green) while the SCI 2010 is displayed on a screen, and display a needle portion 2002 detected from a combined image 2020 by using a second color (for example, red) while the combined image 2020 is displayed on the screen.

Figure 21:
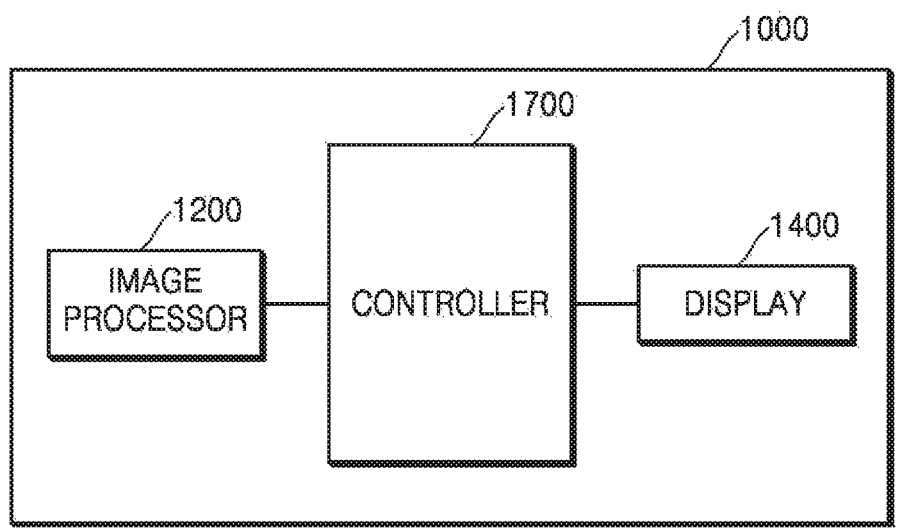
FIGS. 21 and 22 are block diagrams for explaining a configuration of an ultrasound apparatus according to an embodiment.
Figure 22:
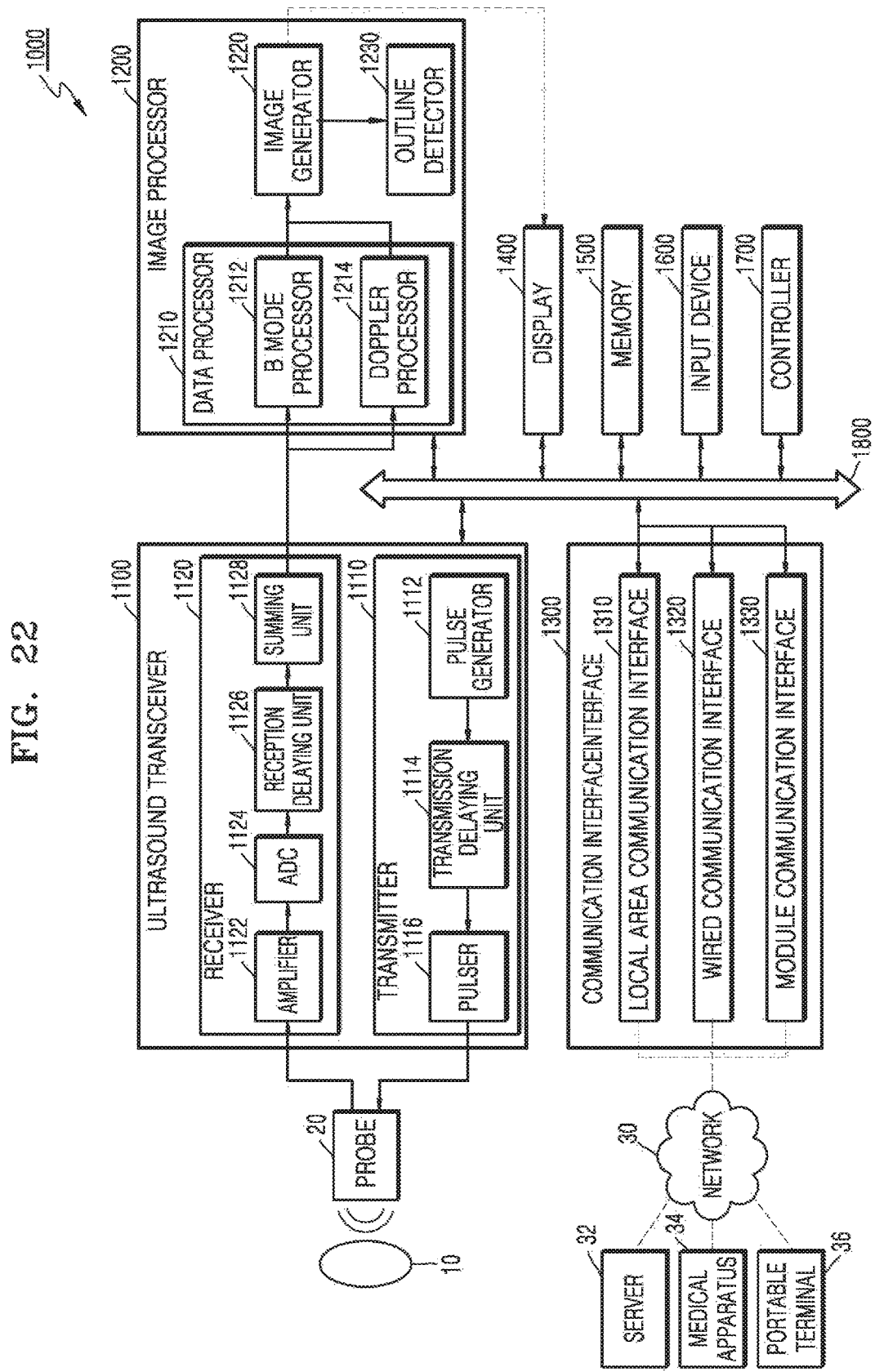

FIGS. 21 and 22 are block diagrams for explaining a configuration of an ultrasound apparatus 1000 according to an embodiment.

As illustrated in FIG. 21, the ultrasound apparatus 1000 according to an embodiment may include an image processor 1200, a display 1400, and a controller 1700. However, the ultrasound apparatus 1000 may be implemented by using a number of components greater than a number of illustrated components, and may be implemented by using a number of components less than a number of illustrated components.

Referring to FIG. 22, the ultrasound apparatus 1000 may include a probe 20, an ultrasound transceiver 1100, an image processor 1200, a communication interface 1300, a display 1400, a memory 1500, an input device 1600, and a controller 1700, which may be connected to one another via buses 1800.

The ultrasound apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound apparatus 1000 by wire or wirelessly, and according to embodiments, the ultrasound apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 124 by delay times necessary for determining reception directionality, and the summing unit 1128 generates ultrasound data by summing the echo signals processed by the reception delaying unit 1166. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 in a data processor 1210 extracts a B mode component from ultrasound data and processes the same. An image generator 1220 may generate an ultrasound image indicating signal intensities as brightness based on the extracted B mode components 1212.

Likewise, a Doppler processor 1214 in the data processor 1210 may extract a Doppler component from ultrasound data, and the image generator 1220 may generate a Doppler image expressing movement of an object in color or a waveform based on the extracted Doppler component.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

The image processor 1200 may obtain a plurality of steering images corresponding to a plurality of steering angles. The plurality of steering images may include first steering images (SCI steering images) corresponding to first steering angles (SCI angles) defined in advance used for generating an SCI.

The image processor 1200 may further obtain an SCI by using the first steering images. Also, the image processor 1200 may generate a needle ultrasound image by combining a steering image obtained at a detected steering angle with an SCI. For example, the ultrasound apparatus 1000 may select a portion in which the needle 30 is displayed from among a steering image, and generate a needle ultrasound image by overlapping the selected portion above an SCI.

The image processor 1200 may include an outline detector 1230 for detecting a needle in each of the plurality of steering images. For example, the outline detector 1230 may detect the outline of a medical tool (for example, a needle) in each of the plurality of steering images based on a difference between the plurality of steering images. Since the brightness value of the needle 30 changes depending on a steering angle, the ultrasound apparatus 1000 may detect the outline of the needle 30 by comparing the plurality of steering images.

A display 1400 displays the generated ultrasound image. The display 1400 may display not only an ultrasound image, but also various pieces of information processed by the ultrasound apparatus 1000 on a screen image via a graphical user interface (GUI). In addition, the ultrasound apparatus 1000 may include two or more displays 1400 according to embodiments.

For example, the display 1400 may display an SCI. Also, the display 1400 may display a needle ultrasound image obtained by using a detected steering angle.

Meanwhile, in the case where the display 1400 and a touchpad form a layered structure and thus are configured as a touchscreen, the display 1400 may serve as an input unit as well as an output unit. The display 1400 may include at least one of a liquid crystal display, a thin film transistor-liquid crystal display, an organic light-emitting diode, a flexible display, a 3D display, and an electrophoretic display. Also, depending on an implementation form of the ultrasound apparatus 1000, the ultrasound apparatus 1000 may include two or more displays 1400.

The communication interface 1300 is connected to a network 30 by wire or wirelessly to communicate with an external device or a server 32. The communication interface 1300 is connected to the network 30 by wire or wirelessly to exchange data with a medical apparatus 34 or a portable terminal 36.

The communication interface 1300 may exchange data with a hospital server or another medical apparatus in a hospital, which is connected thereto via a PACS. Furthermore, the communication interface 1300 may perform data communication according to the digital imaging and communications in medicine (DICOM) standard.

The communication interface 1300 may transmit or receive data related to diagnosis of an object, e.g., an ultrasound image, ultrasound data, and Doppler data of the object 10, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication interface 1300 may receive information about a diagnosis history or medical treatment schedule of a patient from the server 32 and utilizes the received information to diagnose the patient. Furthermore, the communication interface 1300 may perform data communication not only with a server or a medical apparatus in a hospital, but also with a portable terminal of a medical doctor or patient.

The communication interface 1300 may include one or more components for communication with external devices. For example, the communication interface 1300 may include a local area communication interface 1310, a wired communication interface 1320, and a mobile communication interface 1330.

The local area communication interface 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication interface 1320 refers to a module for communication using electric signals or optical signals. Examples of wired communication techniques according to an embodiment may include communication via a twisted pair cable, a coaxial cable, an optical fiber cable, and an Ethernet cable.

The mobile communication interface 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound apparatus 1000. For example, the memory 1500 may store medical data related to diagnosis of an object, such as ultrasound data and an ultrasound image that are input or output, and may also store algorithms or programs which are to be executed in the ultrasound apparatus 1000.

The memory 1500 may be any of various storage media, e.g., a flash memory, a hard disk drive, EEPROM, etc. Furthermore, the ultrasound apparatus 1000 may utilize web storage or a cloud server that performs the storage function of the memory 1500 online.

The input device 1600 refers to a means via which a user inputs data for controlling the ultrasound apparatus 1000. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound apparatus 1000. In other words, the controller 1700 may control operations among the probe 20, the ultrasound transceiver 1100, the image processor 1200, the communication interface 1300, the display 1400, the memory 1500, and the input device 1600 shown in FIG. 1.

All or some of the probe 20, the ultrasound transceiver 1100, the image processor 1200, the communication interface 1300, the display 1400, the memory 1500, the input device 1600, and the controller 1700 may be implemented as software modules. Furthermore, at least one selected from the ultrasound transceiver 1100, the image processor 1200, and the communication interface 1300 may be in the controller 1600. However, embodiments of the present invention are not limited thereto.

The controller 1700 may select one steering image from among a plurality of steering images based on brightness information of the needle 30 in each of the plurality of steering images, and detect a steering angle corresponding to the selected steering image. In this case, the brightness information may be at least one of a brightness value, an intensity value, and an intensity change degree value, but is not limited thereto.

The controller 1700 may select a steering image including the needle 30 having a brightness value greater than the threshold value from among the plurality of steering images.

The controller 1700 may select a new steering angle different from SCI angles when the brightness value of the needle 30 in each of SCI steering images is equal to or less than the threshold value, and generate a needle ultrasound image by using the new steering angle when the brightness value of the needle 30 in a steering image corresponding to the new steering angle is greater than the threshold value.

The controller 1700 may select a fourth steering image including the needle 30 having a highest brightness value from among the plurality of steering images, and select a fifth steering angle within a predetermined angle range from a fourth steering angle corresponding to the fourth steering image in the case where the brightness value of the needle 30 in the fourth steering image is equal to or less than the threshold value. In this case, the predetermined angle range may increase when an angle of the fourth steering image reduces, and may reduce when the angle of the fourth steering image increases.

When the brightness value of the needle 30 in a fifth steering image corresponding to the fifth steering angle is greater than the threshold, the controller 1700 may control the display 1400 to display a fifth needle ultrasound image obtained by using the fifth steering angle.

The controller 1700 may update a needle ultrasound image in real-time by using a detected steering angle. The controller 1700 may determine a new steering angle in the case where the brightness value of the needle in the updated needle ultrasound image is equal to or less than the threshold. For example, the controller 1700 may determine a new steering angle within a predetermined angle range from the detected steering angle. The controller 1700 may control the display 1400 to display a new needle ultrasound image corresponding to the new steering angle.

Methods according to embodiments may be embodied in the form of program commands executable through various computer means, which may be recorded on a non-transitory computer-readable recording medium. The non-transitory computer-readable recording medium may include program commands, data files, and data structures either alone or in combination. The program commands recorded on the non-transitory computer-readable recording medium may be those that are especially designed and configured for the inventive concept, or may be those that are known and available to computer programmers skilled in the art. Examples of the non-transitory computer-readable recording medium include magnetic recording media such as hard disks, floppy disks, and magnetic tapes, optical recording media such as CD-ROMs and DVDs, magneto-optical recording media such as optical disks, and hardware devices such as ROMs, RAMs, and flash memories that are especially configured to store and execute program commands. Examples of the program commands include machine language codes that may be generated by a compiler, and high-level language codes that may be executed by a computer by using an interpreter.

According to an embodiment, the ultrasound apparatus 1000 may provide an ultrasound image in which a medical tool (for example, a needle) clearly appears by adaptively detecting a steering angle.

Though embodiments have been described in detail in the above, the scope of the inventive concept is not limited thereto and it will be understood by a person of ordinary skill in the art that various changes in form and details may be made therein without departing from the spirit and scope as defined by the following claims.

What is claimed is:

1. A method of providing an ultrasound image comprising a medical tool that is inserted into an object, performed by an ultrasound apparatus, the method comprising:
   obtaining a plurality of steering images corresponding to a plurality of steering angles;
   selecting one of the plurality of steering images based on brightness information of the medical tool in each of the plurality of steering images;
   detecting a steering angle corresponding to the one of the plurality of steering images;
   obtaining the ultrasound image comprising the medical tool by using the detected steering angle; and
   displaying the obtained ultrasound image on a screen,
   wherein the selecting the one of the plurality of steering images comprises:
      selecting a first steering image comprising the medical tool having a highest brightness value from among the plurality of steering images,
      when a brightness value of the medical tool in the first steering image is equal to or less than a threshold value, selecting a second steering angle within a particular angle range based on a first steering angle corresponding to the first steering image, and
      when a brightness value of the medical tool in a second steering image corresponding to the second steering angle is greater than the threshold value, selecting the second steering image.

2. The method of claim 1, wherein the obtaining of the plurality of steering images comprises:
   obtaining third steering images corresponding to third steering angles defined in advance and used for generating a spatial compound image.

3. The method of claim 2, wherein the obtaining of the plurality of steering images further comprises:
   obtaining the spatial compound image based on the third steering images.

4. The method of claim 3, wherein the obtaining of the ultrasound image comprises:
   generating the ultrasound image comprising the medical tool by combining a steering image obtained at the detected steering angle with the spatial compound image.

5. The method of claim 2, wherein the selecting of one of the plurality of steering images comprises:
   when a brightness value of the medical tool in each of the third steering images is equal to or less than the threshold value, selecting a fourth steering angle different from the third steering angles; and
   when a brightness value of the medical tool in a fourth steering image corresponding to the fourth steering angle is greater than the threshold value, selecting the fourth steering image, and
   the displaying of the obtained ultrasound image comprises:
   displaying the ultrasound image obtained at the second steering angle.

6. The method of claim 5, wherein the selecting of one of the plurality of steering images further comprises:
   when the brightness value of the medical tool in the fourth steering image is equal to or less than the threshold value, selecting a fifth steering angle different from the third steering angles and the fourth steering angle; and
   when a brightness value of the medical tool in a fifth steering image corresponding to the fifth steering angle is greater than the threshold value, selecting the fifth steering image.

7. The method of claim 1, wherein the selecting of one of the plurality of steering images comprises:
   selecting candidate steering images comprising the medical tool having a brightness value greater than the threshold value from among the plurality of steering images, based on the brightness information of the medical tool in each of the plurality of steering images; and
   selecting one steering image comprising the medical tool having a highest brightness value from among the candidate steering images.

8. The method of claim 1, wherein the selecting of one of the plurality of steering images comprises:
   selecting one steering image comprising the medical tool having a highest brightness value, based on the brightness information of the medical tool in each of the plurality of steering images.

9. The method of claim 1, wherein the obtaining of the ultrasound image comprises:
   selecting a third steering image and a fourth steering image each comprising the medical tool having a brightness value greater than a first threshold value and less than a second threshold value from among the plurality of steering images;
   determining a particular steering angle between a third steering angle corresponding to the third steering image and a fourth steering angle corresponding to the fourth steering image; and
   obtaining the ultrasound image comprising the medical tool by using the determined particular steering angle.

10. The method of claim 1, wherein
    the displaying of the obtained ultrasound image comprises:
    displaying the ultrasound image obtained at the second steering angle.

11. The method of claim 1, wherein the particular angle range increases when an angle of the first steering image decreases and decreases when the angle of the first steering image increases.

12. The method of claim 1, wherein the obtaining of the plurality of steering images comprises:
    detecting an outline of the medical tool in each of the plurality of steering images based on a difference between the plurality of steering images.

13. The method of claim 1, wherein the displaying of the obtained ultrasound image comprises:
    updating the ultrasound image in real-time based on the detected steering angle.

14. The method of claim 13, further comprising:
    when a brightness value of the medical tool in the updated ultrasound image is equal to or less than the threshold value, determining a new steering angle; and
    displaying a new ultrasound image corresponding to the new steering angle.

15. The method of claim 14, wherein the determining of the new steering angle comprises:
    selecting the new steering angle within a predetermined angle range based on the detected steering angle.

16. An ultrasound apparatus for providing an ultrasound image comprising a medical tool inserted into an object, the ultrasound apparatus comprising:
    an image processor configured to obtain a plurality of steering images corresponding to a plurality of steering angles;
    a controller configured to select one of the plurality of steering images based on brightness information of the medical tool in each of the plurality of steering images, detect a steering angle corresponding to the one of the plurality of steering images, and obtain the ultrasound image comprising the medical tool based on the detected steering angle; and a display configured to display the obtained ultrasound image comprising the medical tool, wherein the controller is further configured to:
- select a first steering image comprising the medical tool having a highest brightness value from among the plurality of steering images,
- when a brightness value of the medical tool in the first steering image is equal to or less than a threshold value, select a second steering angle within a particular angle range based on a first steering angle corresponding to the first steering image, and
- when a brightness value of the medical tool in a second steering image corresponding to the second steering angle is greater than the threshold value, select the second steering image.

17. The ultrasound apparatus of claim 16, wherein the plurality of steering images comprises:
third steering images corresponding to third steering angles defined in advance and used for generating a spatial compound image.

18. The ultrasound apparatus of claim 17, wherein the image processor is further configured to obtain the spatial compound image based on the third steering images.

19. The ultrasound apparatus of claim 18, wherein the image processor is further configured to generate the ultrasound image comprising the medical tool by combining a steering image obtained at the detected steering angle with the spatial compound image.

20. The ultrasound apparatus of claim 17, wherein the controller is further configured to select a fourth steering angle different from the third steering angles when a brightness value of the medical tool in each of the third steering images is equal to or less than a threshold value, and to generate a fourth ultrasound image based on the fourth steering angle when a brightness value of the medical tool in a fourth steering image corresponding to the fourth steering angle is greater than the threshold value.

21. The ultrasound apparatus of claim 16, wherein the controller is further configured to select candidate steering images comprising the medical tool having a brightness value greater than a threshold value from among the plurality of steering images based on the brightness information of the medical tool in each of the plurality of steering images, and to select one steering image comprising the medical tool having a highest brightness value from among the candidate steering images.

22. The ultrasound apparatus of claim 16, wherein the controller is further configured to select one steering image comprising the medical tool having a highest brightness value based on the brightness information of the medical tool in each of the plurality of steering images.

23. The ultrasound apparatus of claim 16, wherein the controller is further configured to select a third steering image and a fourth steering image each comprising the medical tool having a brightness value greater than a first threshold value and less than a second threshold value from among the plurality of steering images, to determine a particular steering angle between a third steering angle corresponding to the third steering image and a fourth steering angle corresponding to the fourth steering image, and to obtain the ultrasound image comprising the medical tool based on the determined particular steering angle.

24. The ultrasound apparatus of claim 16, wherein the particular angle range increases when an angle of the first steering image decreases and decreases when the angle of the first steering image increases.

25. The ultrasound apparatus of claim 16, wherein the image processor comprises an outline detector configured to detect an outline of the medical tool in each of the plurality of steering images based on a difference between the plurality of steering images.

26. The ultrasound apparatus of claim 16, wherein the controller is further configured to update the ultrasound image in real-time based on the detected steering angle.

27. The ultrasound apparatus of claim 26, wherein the controller is further configured to determine a new steering angle when a brightness value of the medical tool in the updated ultrasound image is equal to or less than a threshold value and to control the display to display a new ultrasound image corresponding to the new steering angle.

28. The ultrasound apparatus of claim 27, wherein the controller is further configured to determine the new steering angle within a predetermined angle range based on the detected steering angle.

29. A non-transitory computer-readable recording medium having recorded thereon a program for implementing the method of providing the ultrasound image of claim 1.

* * * * *